United States Patent
Wada

(10) Patent No.: US 10,536,651 B2
(45) Date of Patent: Jan. 14, 2020

(54) INSPECTION APPARATUS, METHOD FOR CONTROLLING INSPECTION APPARATUS, AND PROGRAM

(71) Applicant: CANON KABUSHIKI KAISHA, Tokyo (JP)

(72) Inventor: Manabu Wada, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 196 days.

(21) Appl. No.: 15/656,587

(22) Filed: Jul. 21, 2017

(65) Prior Publication Data

US 2018/0041720 A1 Feb. 8, 2018

(30) Foreign Application Priority Data

Aug. 3, 2016 (JP) .................................. 2016-152565
Aug. 3, 2016 (JP) .................................. 2016-152781

(51) Int. Cl.
| | |
|---|---|
| *H04N 5/349* | (2011.01) |
| *H04N 3/08* | (2006.01) |
| *A61B 3/14* | (2006.01) |
| *A61B 3/00* | (2006.01) |
| *G06T 7/00* | (2017.01) |

(52) U.S. Cl.
CPC ............ *H04N 5/349* (2013.01); *A61B 3/0008* (2013.01); *A61B 3/14* (2013.01); *H04N 3/08* (2013.01); *G06T 7/0012* (2013.01); *G06T 2207/30041* (2013.01)

(58) Field of Classification Search
CPC . H04N 5/349; H04N 3/08; A61B 3/14; A61B 3/0008; G06T 7/0012; G06T 2207/30041
See application file for complete search history.

(56) References Cited

U.S. PATENT DOCUMENTS

2009/0303438 A1* 12/2009 Yamada ................. A61B 3/102
  351/206
2010/0277692 A1* 11/2010 Mukai ................. A61B 3/0025
  351/208

(Continued)

FOREIGN PATENT DOCUMENTS

JP  2014068703 A  4/2014

*Primary Examiner* — Mekonnen D Dagnew
(74) *Attorney, Agent, or Firm* — Rossi, Kimms & McDowell LLP

(57) ABSTRACT

An inspection apparatus includes: a first scanning member scanning an object by reciprocating illumination light in a main scanning direction; a second scanning member scanning the object at a constant speed in a sub-scanning direction; a scanning control unit allowing the first and second scanning members to perform 2D scans of the object with the illumination light in first and second fields within a data acquisition area; and a data acquisition unit acquiring data based on the illumination light returned from the first and second fields. The scanning control unit sets the second field by shifting the first field by a predetermined amount in the sub-scanning direction, the predetermined amount determined such that the closer to the scanning center in the main scanning direction within the data acquisition area, the more regular the interval between the first and second fields in the sub-scanning direction.

18 Claims, 13 Drawing Sheets

(56) References Cited

U.S. PATENT DOCUMENTS

2012/0249957 A1* 10/2012 Shibata ............... A61B 3/0025
351/206
2014/0204338 A1* 7/2014 Murase ................. A61B 3/102
351/206

* cited by examiner

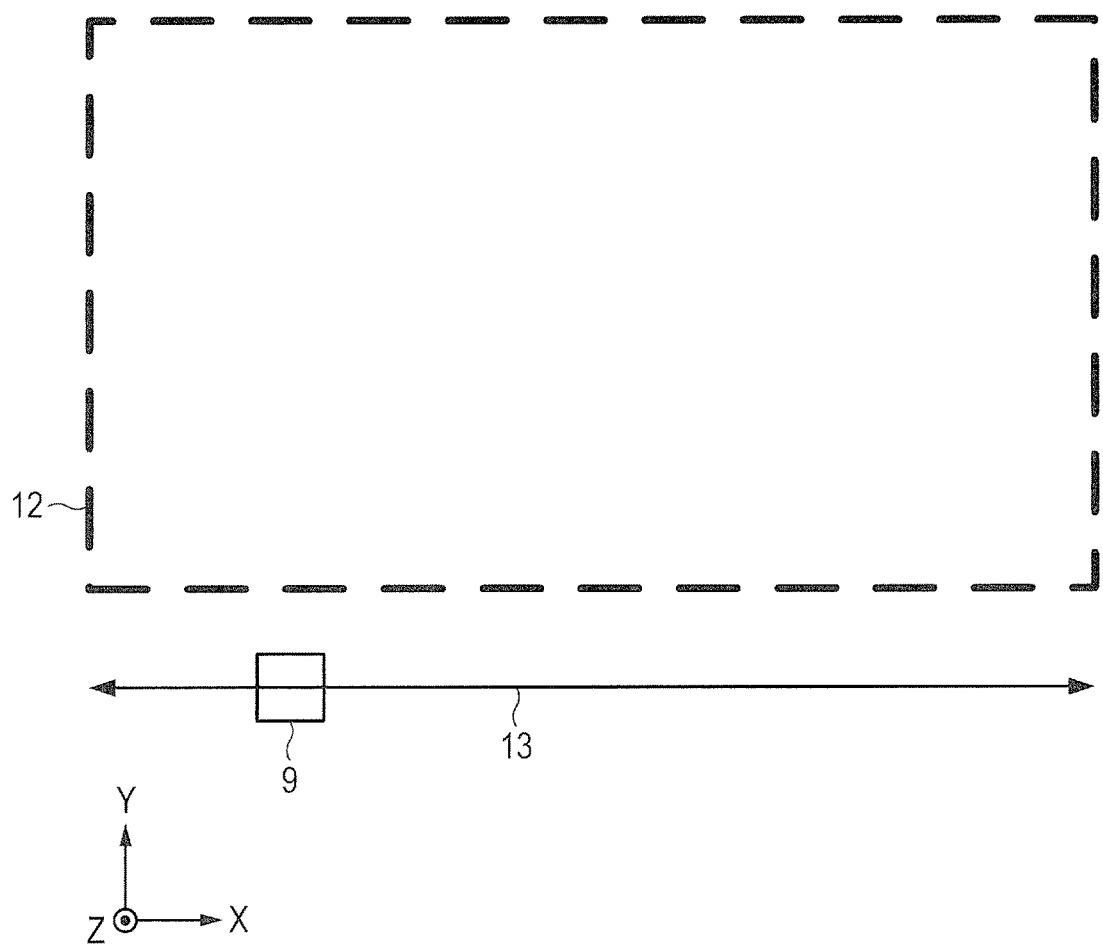

INSPECTION APPARATUS, METHOD FOR CONTROLLING INSPECTION APPARATUS, AND PROGRAM

BACKGROUND OF THE INVENTION

Field of the Invention

The present invention relates to an inspection apparatus which scans an object to be inspected with light to obtain data of the object, a method for controlling the inspection apparatus, and a program.

Description of the Related Art

As one of inspection apparatuses, a scanning laser ophthalmoscope (SLO) is currently applied to obtain data such as images of an eye to be inspected. An ophthalmic imaging apparatus (one aspect of the inspection apparatus) typified by the SLO uses a scanning optical system including two kinds of scanners to perform a 2D scan of the eye to be inspected with illumination light, thereby obtaining an image. In this event, the apparatus typically uses a resonant scanner (resonance type scanner) in a main scanning direction of the 2D scan and a galvano scanner in a sub-scanning direction.

Such an ophthalmic imaging apparatus typified by the SLO has recently been required to have a higher resolution. At the same time, the ophthalmic imaging apparatus has been required to achieve a higher frame rate and a higher refresh rate throughout operations from data acquisition to image generation for the purpose of enabling a good diagnosis of an eye to be inspected, and also to provide a high-resolution less distorted image for use in actually inspecting the eye fundus in detail. A configuration disclosed in Japanese Patent Application Laid-Open No. 2014-68703, including a resonant scanner and a galvano scanner, accomplishes a higher resolution by performing reciprocating scanning with the resonant scanner to increase the number of pixels captured in one frame.

Meanwhile, as for a deviation between the data acquisition position on the eye fundus and the corresponding pixel on the display screen to be described later, two pieces of data acquired at two positions on a sub-scanning line are used for calculation to obtain data of a pixel which is located at a middle position between the two data acquisition positions and has no corresponding data. This eliminates the necessity to consider the displacement between the data acquisition position and the corresponding pixel, and provides an image with no distortion.

Here, the reciprocating scanning means acquisition of information in both of forward scanning and backward scanning during scanning with the illumination light moved in the main scanning direction. Also, a higher frame rate means an increase in frame rate expressed by the number of frames per unit time at which one image to be displayed on a display screen is generated from data. A higher refresh rate means an increase in refresh rate equivalent to a replacement speed in continuous display of images on the display screen as a moving image, for example, at which a first image for one timing is replaced by a second image for the next timing.

The eye to be inspected repeats motion called involuntary eye movement. Thus, for image acquisition, it is required to detect the involuntary eye movement of the eye to be inspected and to perform eye fundus tracking which is to correct the scanning position of the illumination light in response to the involuntary eye movement. In this event, in order to quickly respond to the involuntary eye movement, it is important to improve the responsiveness of the eye fundus tracking by improving the frame rate and the refresh rate. Moreover, actual inspection also requires provision of a moving image with less flicker and good visibility. From this viewpoint, again, there are needs for a higher frame rate and a higher refresh rate in data acquisition for image generation and in the image generation.

Note that, as described above, the ophthalmic imaging apparatus often performs scanning with the illumination light in the main scanning direction with the resonant scanner and performs scanning with the illumination light in the sub-scanning direction with the galvano scanner. As described in Japanese Patent Application Laid-Open No. 2014-68703, it is required to also pay attention to image distortion for improving the resolution by the reciprocating scanning with the resonant scanner. Therefore, in order for an inspector to perform inspection without feeling strangeness during observation of an eye fundus image, data acquisition of the object to be inspected such as the eye fundus is required to improve the visibility of an image against the distortion.

Moreover, the configuration disclosed in Japanese Patent Application Laid-Open No. 2014-68703 makes no mention of the interlaced scanning. Therefore, there is also no suggestion about point to note in generation of images from data acquired by the interlaced scanning. As a measure against the deviation between the data acquisition position and the corresponding pixel described above, the technology disclosed in Japanese Patent Application Laid-Open No. 2014-68703 uses data at two data acquisition positions at an equal distance in the sub-scanning direction from the location of the pixel for which the data is to be calculated. Thus, when the distance between the two pieces of data is increased, the obtained data of the pixel may fail to reflect an actual state, and result in generation of a so-called blurred image.

SUMMARY OF THE INVENTION

In consideration of the above circumstances, the present invention provides an inspection apparatus which obtains data of an object to be inspected with less distortion and good visibility even in the case of improving both of the resolution and frame rate.

Alternatively, the present invention provides an inspection apparatus with improved frame rate for generating an image of an object to be inspected with less image distortion by scanning with illumination light.

An inspection apparatus according to one aspect of the present invention to solve the foregoing problems includes:

a first scanning member that scans an object to be inspected by reciprocating scanning with illumination light in a main scanning direction;

a second scanning member that scans the object to be inspected at a constant speed with the illumination light in sub-scanning direction that intersects with the main scanning direction;

a scanning control unit that allows the first and second scanning members to perform a 2D scan of the object to be inspected with the illumination light in a first field within a data acquisition area, and to perform a 2D scan of the object to be inspected in a second field different from the first field within the data acquisition area; and a data acquisition unit that acquires data of the object to be inspected based on the illumination light returned from the object to be inspected in the first and second fields, wherein the scanning control unit sets the second field by shifting a scanning start position of the 2D scan for the first field by a predetermined amount in the sub-scanning direction, and the predetermined amount is determined for the 2D scan with the illumination light such that the closer to the scanning center in the main scanning direction within the data acquisition area, the more regular the interval between the first and second fields in the sub-scanning direction.

Alternatively, an inspection apparatus according to one aspect of the present invention to solve the foregoing problems includes:

a first scanning member that scans an object to be inspected by reciprocating scanning with illumination light in a main scanning direction;

a second scanning member that scans the object to be inspected at a constant speed with the illumination light in a sub-scanning direction that intersects with the main scanning direction;

a scanning control unit that allows the first and second scanning members to perform a 2D scan of the object to be inspected with the illumination light in a first field within a data acquisition area, and to perform a 2D scan of the object to be inspected in a second field different from the first field within the data acquisition area;

an acquisition position setting unit that sets data acquisition positions, in the first and second fields, for acquiring data from the illumination light returned from the object to be inspected;

a selecting unit that selects, in order to generate data at new positions arranged at regular intervals in the sub-scanning direction, the data acquired at least at two data acquisition positions located closest to each of the new positions among the data acquisition positions in the first and second fields; and an image generation unit that generates an image of the object to be inspected by using data at the new positions generated from the selected data.

The present invention can provide an inspection apparatus which acquires data of an object to be inspected with less distortion and good visibility even in the case of improving the resolution and frame rate.

Alternatively, the present invention can provide an inspection apparatus improved frame rate for generating an image of an object to be inspected with reduced image distortion by scanning with illumination light.

Further features of the present invention will become apparent from the following description of exemplary embodiments with reference to the attached drawings.

BRIEF DESCRIPTION OF THE DRAWINGS

FIG. 3 is a diagram explaining scanning of a correction photodiode with illumination light in the configuration shown in FIG. 1.

DESCRIPTION OF THE EMBODIMENTS

Figure 1:
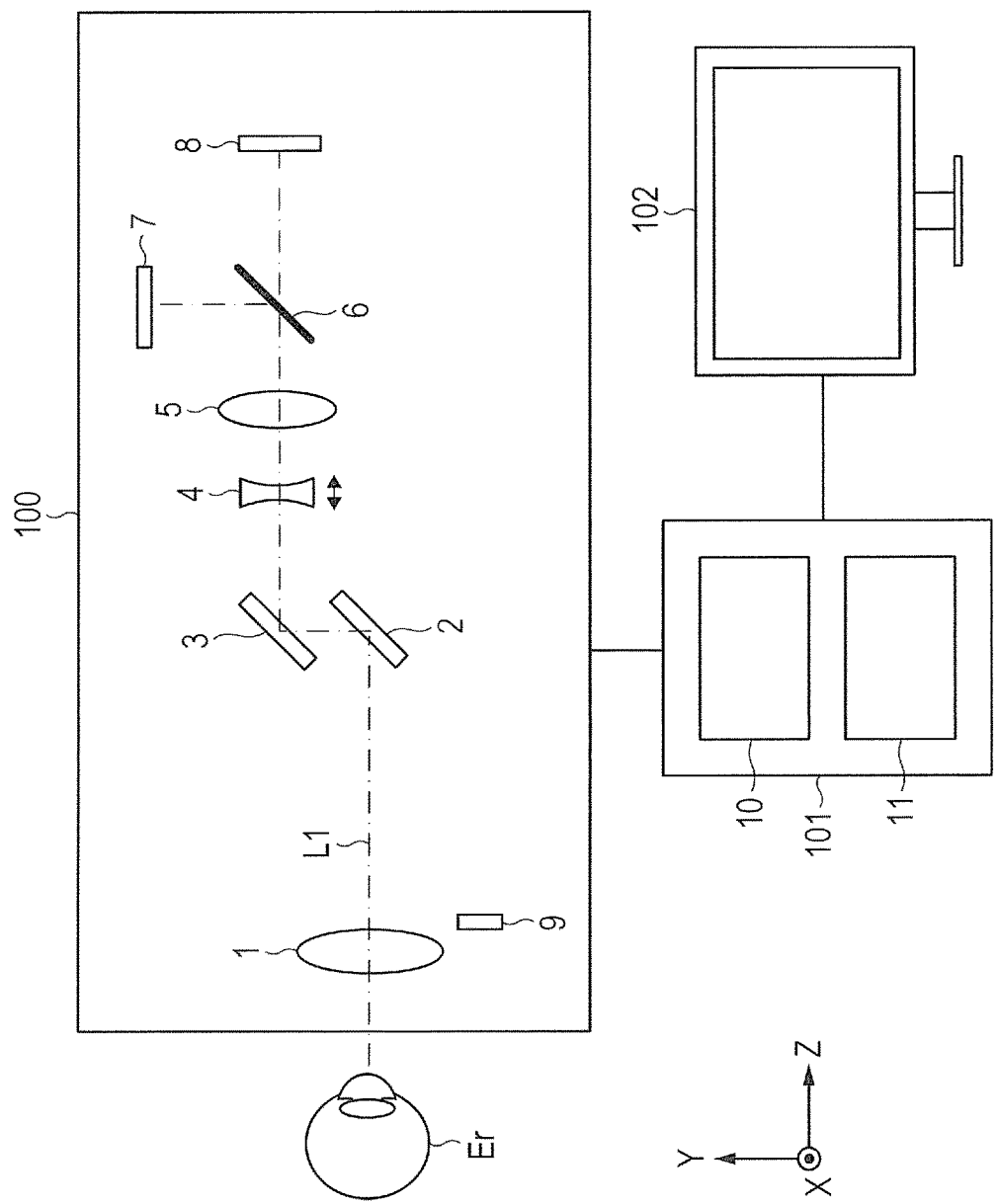
FIG. 1 is a schematic diagram showing a configuration of an SLO according to an embodiment of the present invention.

Preferred embodiments of the present invention will now be described in detail in accordance with the accompanying drawings. However, shapes, relative positions of constituent elements or the like described in the following embodiments are arbitrary and may be changed depending on configurations and various conditions of apparatuses to which the present invention is applied. Also, throughout the drawings, the same reference numerals are used to designate the same or functionally similar elements.

(Embodiment 1)

As described above, in a scanning optical system using a resonant scanner, the resolution is improved by performing reciprocating scanning to obtain information. To also additionally improve the frame rate, it is conceivable to combine the reciprocating scanning with so-called interlaced scanning wherein images are acquired in an odd number field and an even number field, respectively. In Embodiment 1 described below, the interlaced scanning and the reciprocating scanning are performed in combination to achieve a higher resolution and a higher frame rate.

Here, the interlaced scanning with illumination light on the eye fundus, for example, means, when a scanning area is defined in a grid pattern in a main scanning direction (horizontal direction) and a sub-scanning direction (vertical direction), scanning every other line in the main scanning direction, i.e., the first line, the third line, the fifth line, . . . , with the illumination light. The odd number field means a field for scanning of the first, third, fifth, . . . lines, while the even number field means a field for scanning of the second, fourth, sixth, . . . lines. Complete data in the scanning area is acquired by combining data acquired from the two fields. In the case of the reciprocating scanning in the odd number field, the first, fifth, ninth, . . . lines correspond to forward scanning with the illumination light, and the third, seventh, eleventh, . . . lines correspond to backward scanning with the illumination light. Note that, here, for convenience of explanation, it is assumed that the respective lines in the odd number field and the respective lines in the even number field have the same width in the sub-scanning direction. However, the even number field may be set so as to be shifted from the odd number field by a given distance in the sub-scanning direction. In other words, more fields may be additionally set, such as setting a third field, for example, assuming that the odd number field is a first field and the even number field is a second field. That is, although an irradiation position (scanning start position) of the illumination light is shifted in the sub-scanning direction to perform scanning with the illumination light in the next field after completion of scanning with the illumination light in the odd number field, such a shift amount does not have to correspond to one line in the odd number field.

A one frame image is individually generated and obtained from the data acquired in each of the odd number field and the even number field, and the images thus obtained are alternately updated. In the following embodiment, data is acquired from the eye fundus by the interlaced scanning with the illumination light to sequentially generate and update images. By simultaneously acquiring data through both forward scanning and backward scanning with the illumination light, a higher resolution as well as a higher frame rate are achieved. For acquisition of a still image, the same number of pixel data as the number of pixel data acquired by normal reciprocating scanning is acquired by combining the image in the odd number field with the image in the even number field.

FIG. 1 is a schematic diagram showing a configuration of an SLO according to an embodiment of the present invention. Note that the apparatus to which the present invention is applied is not limited to the SLO. For example, the prevent invention is also applicable to an inspection apparatus such as an ophthalmic imaging apparatus which scans an eye to be inspected with illumination light (measurement light), particularly which scans the eye using a resonant scanner, such as an OCT apparatus and an AO-SLO apparatus.

The SLO shown in FIG. 1 includes a data acquisition unit 100, a system unit 101, and a display unit 102. The data acquisition unit 100 acquires data of the eye fundus Er such as luminance information by scanning the eye to be inspected (the eye fundus Er in this embodiment) with the illumination light. The system unit 101 controls the data acquisition unit 100 and generates an SLO image based on the data acquired by the data acquisition unit 100. The display unit 102 displays the SLO image generated by the system unit 101. Note that, in this embodiment, the description is given of, as an example, the configuration in which the respective units are independently arranged. However, the respective units may be integrated as appropriate depending on installation conditions and the like, such as integrating the system unit 101 with the display unit 102. Alternatively, the SLO may be wholly or partly combined with another apparatus such as the OCT apparatus.

First, a configuration of the data acquisition unit 100 is described. On an optical path L1 facing the eye to be inspected, an objective lens 1, a galvano scanner 2, a resonant scanner 3, lenses 4 and 5, a mirror 6, and an SLO light source 8 are sequentially arranged. Also, a photodiode 7 is arranged on a reflected light axis of the mirror 6. These optical elements make up an SLO optical system for the eye fundus Er.

The lens 4 is driven by an unillustrated motor in an optical axis direction indicated by the arrow in FIG. 1 for focusing of the SLO optical system. The SLO light source emits light having a wavelength around 780 nm as illumination light. The photodiode 7 detects light returned from the eye fundus Er irradiated with the illumination light. The mirror 6 includes a prism having metal or the like deposited on a perforated mirror or a hollow mirror, and splits the optical path into two paths, one for the illumination light emitted by the SLO light source 8 and one for the light returned from the eye fundus Er.

The illumination light emitted by the SLO light source 8 passes through the mirror 6 and then through the lenses 5 and 4 before reaching the resonant scanner 3 and the galvano scanner 2 for scanning the eye fundus Er. The light returned from the eye fundus Er is reflected by the mirror 6 and guided to the photodiode 7 after returning the same path as that of the illumination light.

The galvano scanner 2 and the resonant scanner 3 make up a scanning optical system for scanning the eye fundus Er with the illumination light emitted by the SLO light source 8. The resonant scanner 3 scans the eye fundus Er in the main scanning direction (X direction) with the illumination light, while the galvano scanner 2 scans the eye fundus Er in the sub-scanning direction (Y direction) with the illumination light. The resonant scanner 3 can linearly scan the eye fundus Er in the main scanning direction with the illumination light by deflecting the illumination light with a mirror oscillated fast at a resonant frequency. The galvano scanner 2 operates in uniform linear motion so that the light deflected to the main scanning direction by the resonant scanner 3 is further deflected to the sub-scanning direction. The eye fundus Er can be two-dimensionally scanned with the illumination light by the resonant scanner 3 and the galvano scanner 2 as described above.

Note that the resonant scanner 3 generally includes a mirror that reflects the illumination light and a member that oscillates the mirror about the axis. Since the member uses a resonance phenomenon, the scanning speed is increased or decreased when the eye fundus Er is scanned with the illumination light reflected by the mirror. As for the resonant scanner 3, it is known that scanning conditions, such as the resonant frequency (period of oscillation) and amplitude thereof, change as a consequence of environmental changes. In this embodiment, a correction photodiode 9 is provided to detect the scanning conditions of the resonant scanner 3. The correction photodiode 9 is arranged at a position that does not overlap with a scanning area defined by the XY-coordinate plane during a 2D scan of the eye fundus Er with the illumination light by the resonant scanner 3 and the galvano scanner 2. As for the detection of the scanning conditions of the resonant scanner 3 by using the correction photodiode 9, detailed description thereof is given later in conjunction with an image acquisition flow.

The system unit 101 includes a controller 10 that controls the data acquisition unit 100 and an image generator 11 that generates SLO images. The controller 10 controls the galvano scanner 2, the resonant scanner 3, the lens 4, the photodiode 7, the SLO light source 8, and the correction photodiode 9. The image generator 11 generates SLO images based on the data acquired by the photodiode 7. The display unit 102 displays the SLO images generated by the image generator 11.

Figure 2:
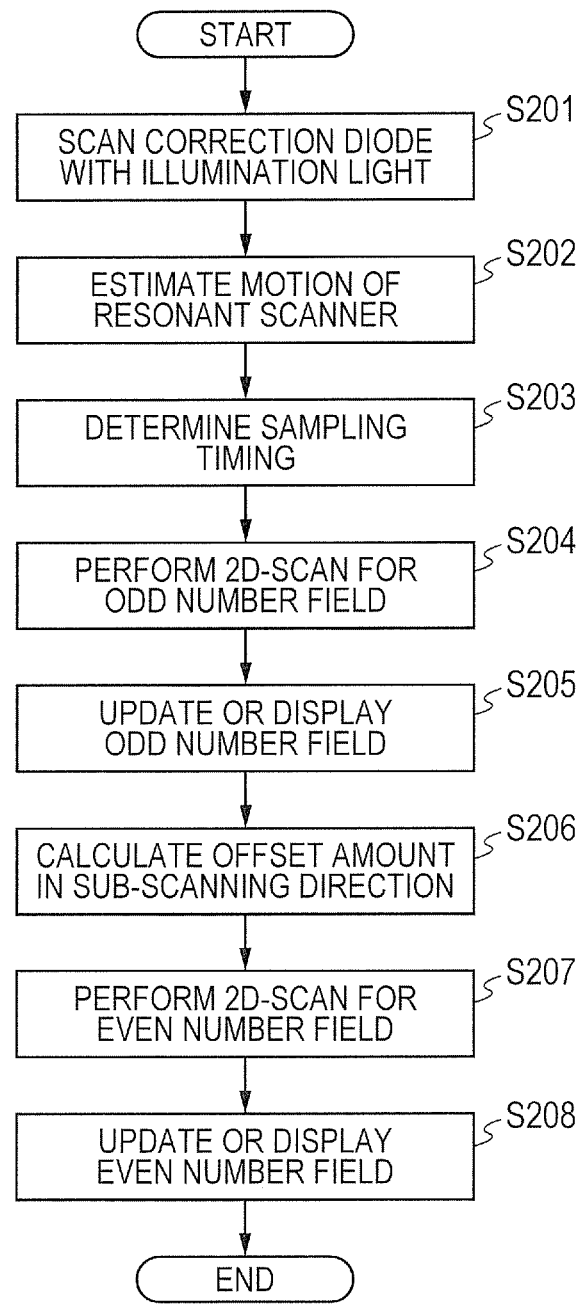
FIG. 2 is a flowchart showing an image acquisition flow according to Embodiment 1.

Next, with reference to a flowchart of FIG. 2, description is given of a flow of steps executed during image acquisition by the SLO including the data acquisition unit 100, the system unit 101, and the display unit 102 described above in Embodiment 1. Also, the respective steps are accordingly described in detail with reference to FIGS. 3 to 8. The flowchart constitutes one aspect of a method for controlling the inspection apparatus according to this embodiment, and respective steps of the flowchart constitute respective steps of the method.

In Step S201, the correction photodiode 9 is scanned with the illumination light by the resonant scanner 3. To be more specific, the controller 10 starts driving the resonant scanner 3 and also positions the galvano scanner 2 at a predetermined angle in the sub-scanning direction corresponding to the correction photodiode 9. Then, the controller 10 drives the SLO) light source 8. Through the above operations, the correction photodiode 9 is scanned more than once in a reciprocating manner in the main scanning direction along a scanning trajectory 13 as shown in FIG. 3 with the illumination light from the SLO light source 8.

Note that FIG. 3 is a diagram explaining the scanning of the correction photodiode 9 with the illumination light. FIG. 3 also shows a relationship between the correction photodiode 9 and a plane corresponding to a data acquisition area of the eye fundus Er on plane perpendicular to the optical axis including the correction photodiode 9. That is, an acquisition area 12 shown in FIG. 3 corresponds to the data acquisition area on the XY-plane during the 2D scan of the eye fundus Er with the illumination light. The correction photodiode 9 is arranged at the position where the scanning trajectory 13 for the 1D scan executed in Step S201 does not overlap with the acquisition area 12 that is the data acquisition area for the 2D scan of the eye fundus Er.

Figures 4A, 4B:
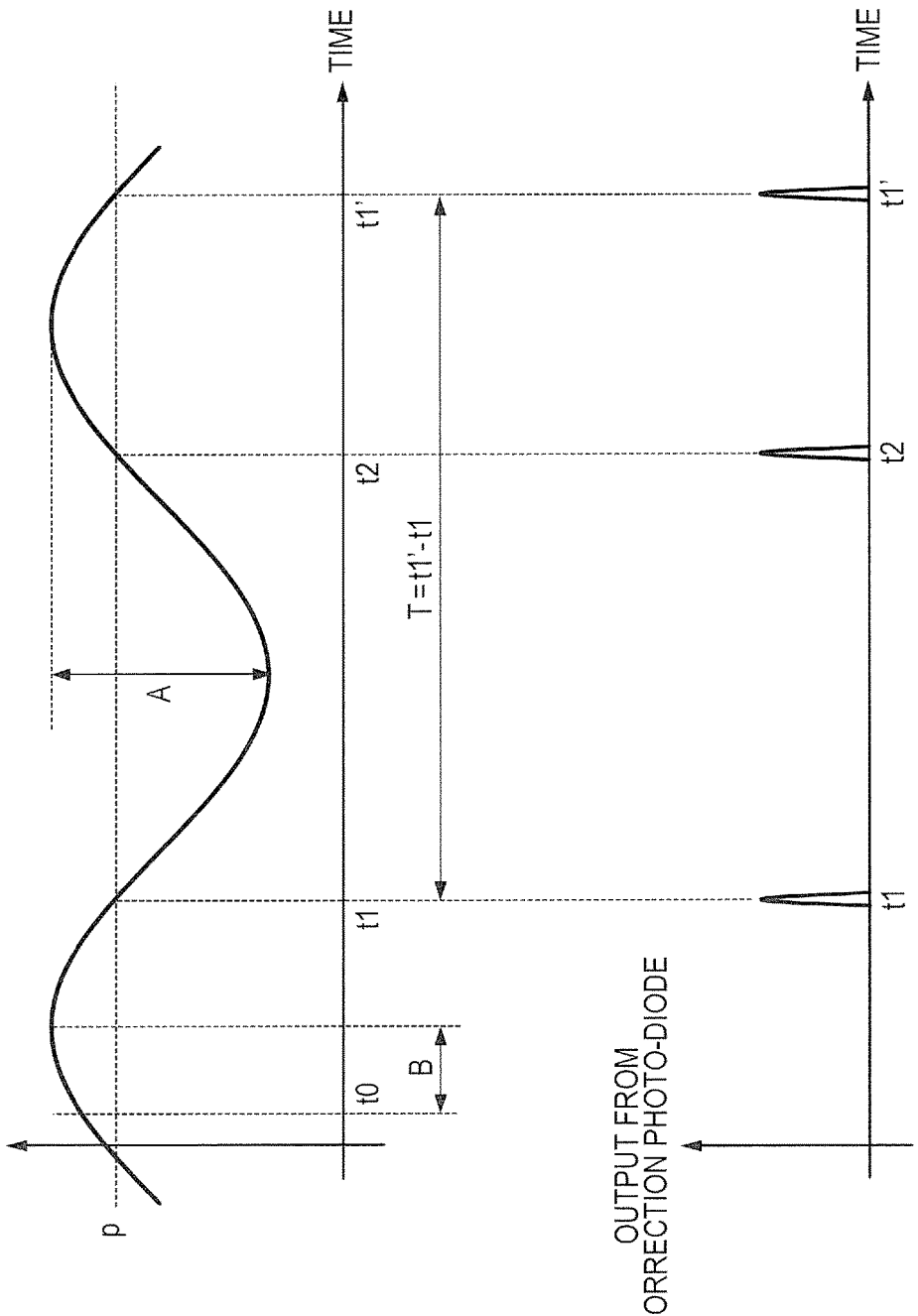
FIGS. 4A and 4B are diagrams showing a relationship between time and scanning positions of a resonant scanner in a main scanning direction in the configuration shown in FIG. 1, and also showing signals outputted by the correction photodiode.

During the scanning with the illumination light on the scanning trajectory 13, a relationship between time and the scanning position of the illumination light in the main scanning direction by the resonant scanner 3 exhibits a sinusoidal pattern as shown in FIG. 4A. While the correction photodiode 9 is scanned more than once in a reciprocating manner with the illumination light in Step S201, FIG. 4A shows a part of the reciprocating scanning thus performed more than once. A point p on the vertical axis in FIG. 4A represents the position of the correction photodiode 9 in the main scanning direction. With reference to FIG. 4A, the correction photodiode 9 receives the illumination light from the SLO light source 8 at timings t1, t2, and t1'. FIG. 4B shows signals outputted upon receipt of the illumination light by the correction photodiode 9.

Next, in Step S202, the controller 10 estimates the motion of the resonant scanner 3 by using the timings t1, t2, and t1' of the signals outputted by the correction photodiode 9 in Step S201. The following equation (1) is used for the estimation.

[Equation 1]

$$Px = A\cos\left(\frac{2\pi}{T}t + B\right) \quad (1)$$

Here, Px represents the scanning position of the resonant scanner 3 in the main scanning direction, A represents the amplitude of the resonant scanner 3, and t represents time. Also, T represents the oscillation period of the resonant scanner 3, which is expressed by T=t1'-t1. Meanwhile, B represents a difference between the timing t0 of a synchronization signal outputted in each period by the resonant scanner 3 and the timing of switching between forward scanning and backward scanning by the resonant scanner 3. The forward scanning and the backward scanning by the resonant scanner 3 are switched at peaks and troughs of the sinusoidal pattern.

The constants A and B described above can be obtained by solving two equations obtained by plugging in (t1, p) and (t2, p) for (t, Px) in the above equation (1). Therefore, the motion of the resonant scanner 3 can be estimated by the equation (1). The correction photodiode 9 and the corresponding module of the controller 10 that detects the period of oscillation of the resonant scanner 3 based on the output from the correction photodiode 9 described above constitute a period detecting unit in this embodiment. Likewise, such configurations constitute an amplitude detecting unit in this embodiment to detect the amplitude of oscillation of the resonant scanner 3.

Next, in Step S203, the controller 10 determines timing of data sampling performed in subsequent Steps S204 and S207. This determination uses the result of the estimation of the motion of the resonant scanner 3 obtained in Step S202 described above. For example, sampling timing for acquiring an SLO image (data) at a point in an unillustrated main scanning direction px1 is obtained by plugging Px=px1 into the equation (1) and solving the equation for t. By performing the above calculation for all positions where data acquisition is desired in the main scanning direction in the one frame SLO image, respectively, sampling timing for acquiring all the data can be obtained. In this embodiment, the sampling timing (data acquisition timing) is determined such that data acquisition positions in the odd number field and the even number field are aligned in a straight line in the sub-scanning direction. Also, the data acquisition positions on the eye fundus are associated with the arrangement of pixels when the SLO image is displayed on the display unit 102 to be described later, based on the estimated motion of the resonant scanner 3.

Next, in Step S204, the controller 10 performs scanning for the odd number field in the interlaced scanning of the eye fundus Er. As described above, from Step S201 to Step S203, the galvano scanner 2 is positioned at the predetermined angle in the sub-scanning direction corresponding to the correction photodiode 9. In Step S204, the galvano scanner 2 is operated in uniform linear motion in the sub-scanning direction so that a 2D scan with the illumination light is performed by the resonant scanner and the galvano scanner 2.

Figure 5:
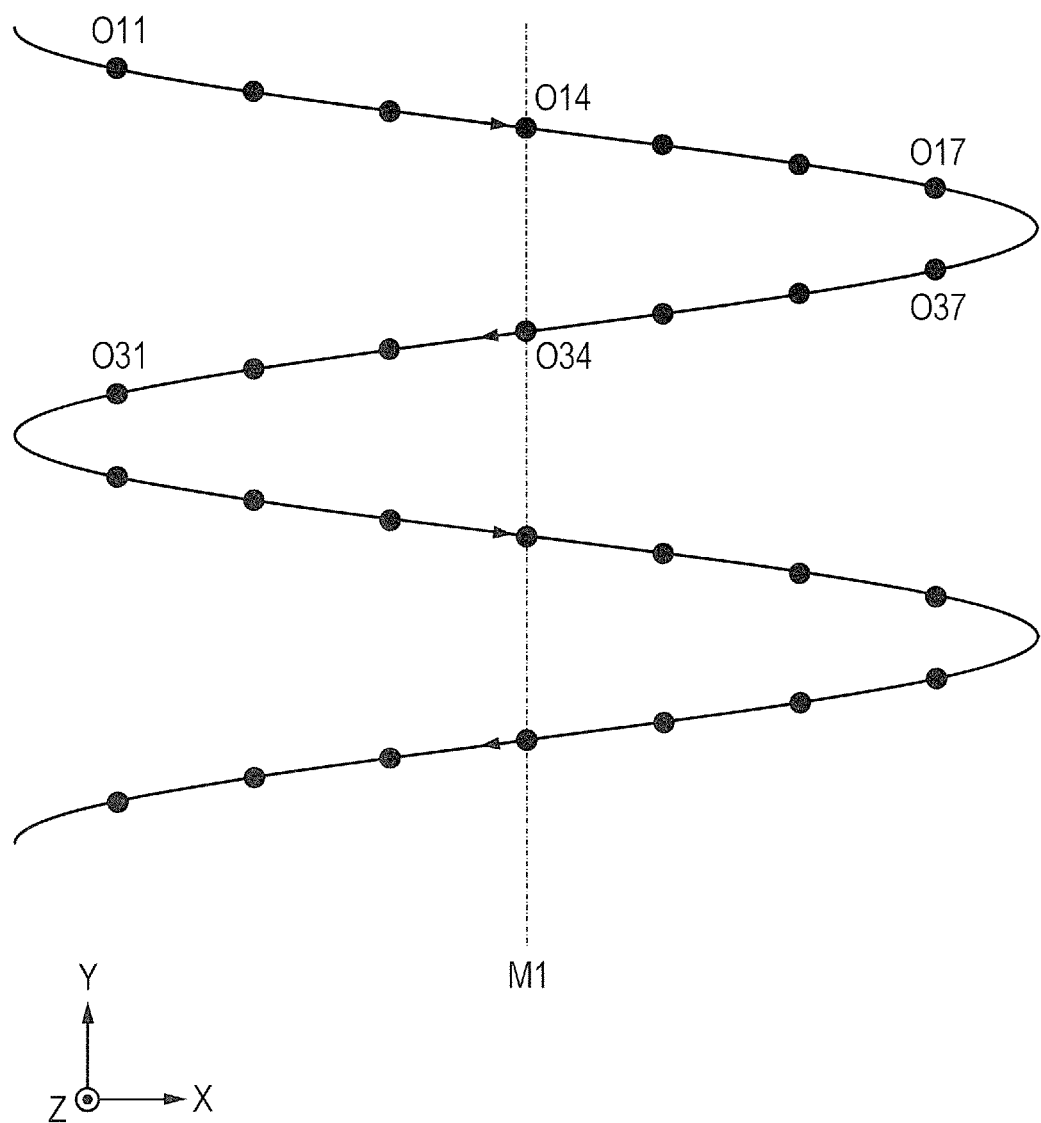
FIG. 5 is a diagram illustrating a scanning trajectory and sampling points in an odd number field.

FIG. 5 illustrates the scanning trajectory and sampling points thereon in the scanning with the illumination light in the odd number field, which is performed in Step S204. In FIG. 5, the scanning trajectory is drawn with a solid line. In FIG. 5, the scanning trajectory indicated by the right-pointing arrow extends from the part to the left of a sampling point O11 to be described later to the part to the right of a sampling point O17. Meanwhile, the scanning trajectory indicated by the left-pointing arrow extends from the part to the right of a sampling point O37 to the part to the left of a sampling point O31. The directions of the arrows in FIG. 5 show that the forward scanning and the backward scanning by the resonant scanner 3 are switched at the right and left ends of the scanning trajectory. Furthermore, the points indicated by black circles in FIG. 5 represent sampling points in the odd number field within the data acquisition area on the eye fundus Er. In FIG. 5, as described above, the presence of the black circles in both of the forward scanning and the backward scanning during the reciprocating scanning shows that the data acquisition is carried out in both of the forward scanning and the backward scanning by the resonant scanner 3. Note that the dashed-dotted line M1 in FIG. 5 represents the center in the main scanning direction in the main scanning area of the illumination light by the resonant scanner 3.

All the sampling points acquired in the odd number field are sampled at regular intervals in the main scanning direction. This is because the sampling timing is calculated in Step S203 such that the desired sampling points can be obtained, and then the sampling is performed based on the calculation. However, the sampling points are not arranged at regular intervals in the sub-scanning direction. This is because the motion of the resonant scanner 3 changes with time in the sinusoidal pattern shown in FIGS. 4A and 4B.

Figure 6:
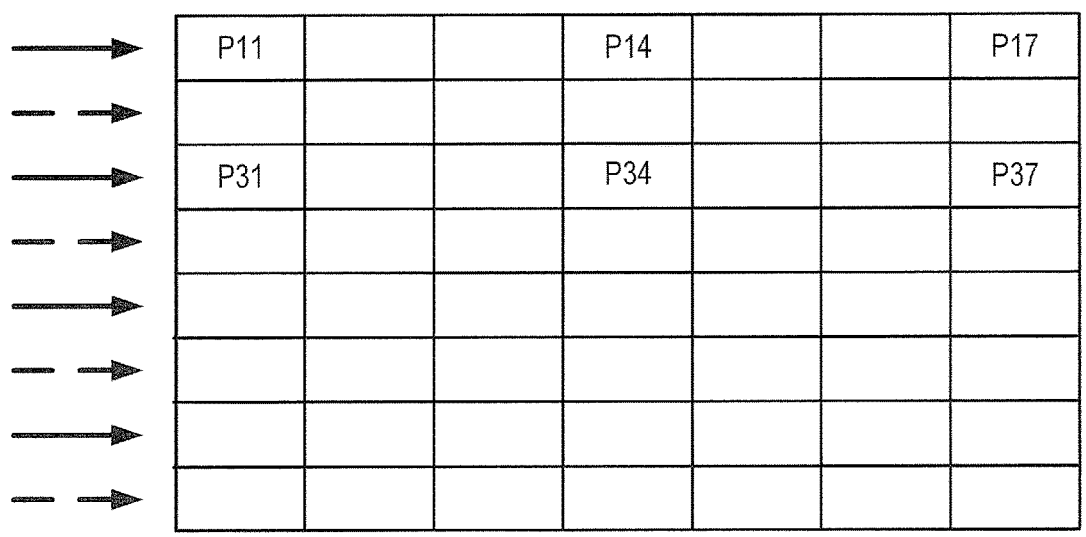
FIG. 6 is a diagram showing a relationship between an SLO image displayed on a display unit shown in FIG. 1 and scanning fields.

In Step S205, the image generator 11 generates an SLO image in the odd number field from the 2D scan data acquired in Step S204. The generated SLO image is displayed on the display unit 102, or the displayed SLO image is updated to the newly generated SLO image. FIG. 6 shows the SLO image displayed on the display unit 102, and pixels in the odd number lines, i.e., the first, third, fifth, . . . , indicated by the solid arrows in FIG. 6 are pixels in the odd number field to be updated.

Here, the data acquired at the sampling point O11 in FIG. 5 is displayed in a pixel P11 in FIG. 6. Likewise, the data acquired at the sampling points O14, O17, O37, O34, and O31 in FIG. 5 are displayed in pixels P14, P17, P37, P34, and P31 in FIG. 6, respectively. Based on the estimation of the motion of the resonant scanner 3 in Step S202, the image generator 11 associates the sampling points with the pixels in the image while determining where the forward scanning and the backward scanning are switched therebetween.

When the data is acquired by the reciprocating scanning and the interlaced scanning with the resonant scanner and the galvano scanner, the image generated from the data may be distorted depending on the relationship between the scanning positions in the odd number field and the even number field. To be more specific, there arises a difference, between the odd number field and the even number field, in deviation amount in the correspondence relationship between the sampling points and the pixels. Consequently, when images obtained from the two fields are alternately displayed, a flicker in the image, a feeling of strangeness or the like occurs in a portion with such a difference. Hereinafter, such a portion with a deviation in the correspondence relationship is referred to as a distorted portion of the image and an increase in difference in deviation amount is referred to as an increase in distortion. Although described in detail later with reference to FIGS. 7 and 8, an attention area such as a diseased area of the eye to be inspected, which is desired to be acquired, is often positioned in the center of the image at an ophthalmic clinic. Therefore, it is not preferable that the center of the image in the main scanning direction is distorted. More specifically, in order to suppress image distortion in the attention area, it is required to appropriately set a shift amount, related to the image distortion, in the sub-scanning direction during switching from the odd number field to the even number field in the interlaced scanning.

In the next Step S206, the controller 10 calculates an appropriate offset amount (the shift amount described above) for setting the even number field during the interlaced scanning. Here, the offset amount means an amount by which the scanning position in the even number field in the sub-scanning direction is offset from the odd number field such that the scanning position in the odd number field and the scanning position in the even number field do not overlap with each other during the interlaced scanning. The offset amount calculated and set in Step S206 allows adjustment of a region where the SLO image generated from the data acquired in the two fields is distorted in the sub-scanning direction. In an example described below, the image is not distorted in the center in the main scanning direction when seen on the pixels displayed on the display unit 102. Note that the offset amount determined in Step S206 is applied in each case of subsequent switching between the odd number field and the even number field.

Figure 7:
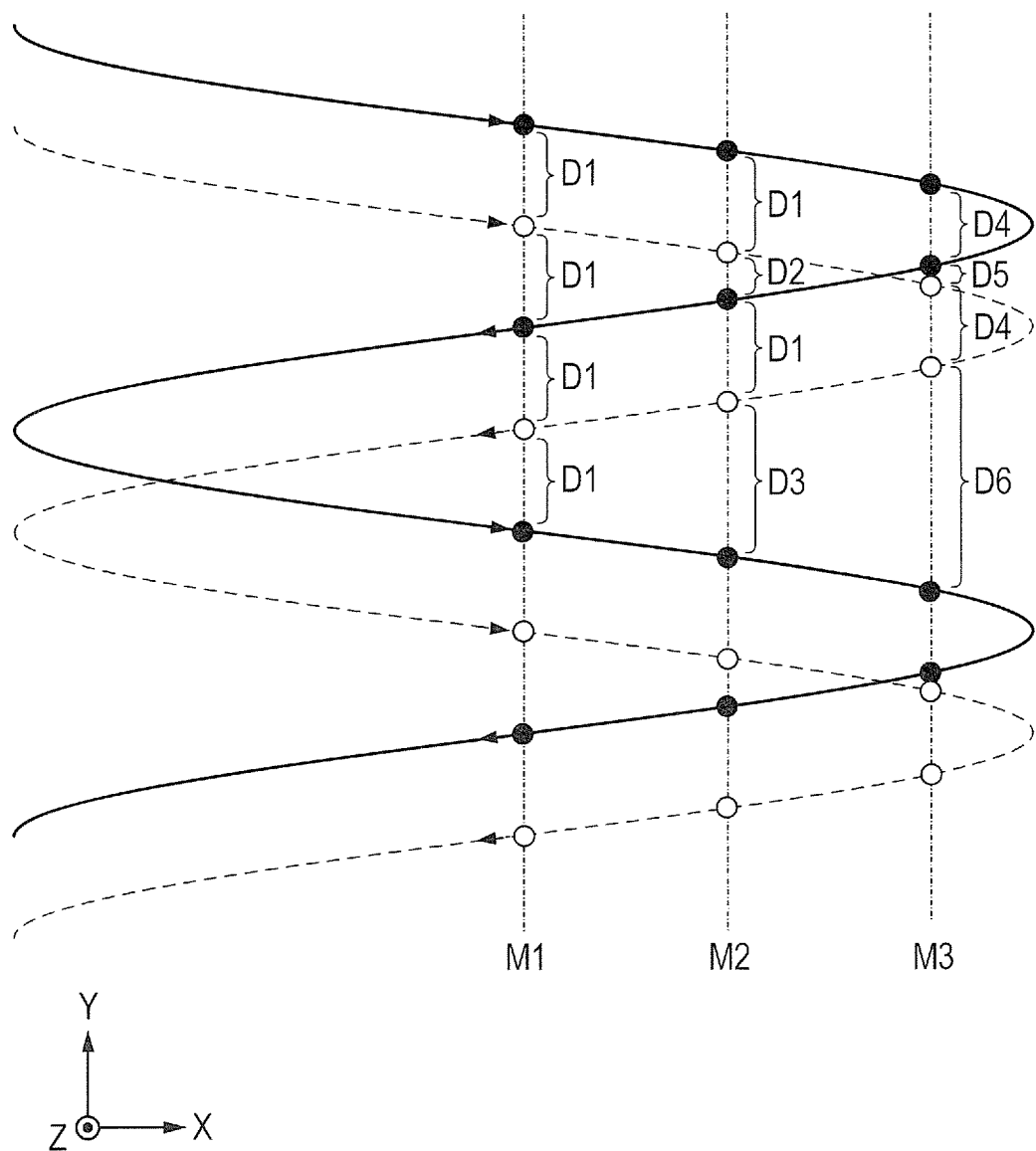
FIG. 7 is a diagram showing a positional relationship between scanning trajectories and sampling points in both fields when an even number field is generated by being shifted from the odd number field by an appropriate offset amount.

FIG. 7 shows scanning trajectories and sampling points in the two fields when the scanning position in the even number field is shifted from the odd number field by an optimum offset amount. In FIG. 7, the scanning trajectory in the odd number field is indicated by a solid line, which is the trajectory of the scanning with the illumination light performed in Step S204. Meanwhile, the scanning trajectory in the even number field is indicated by a broken line. Also, the sampling points in the odd number field and the even number field are indicated by black circles and white circles, respectively. Note that, in the following description, scanning trajectories corresponding to the odd number field are all indicated by solid lines, while scanning trajectories corresponding to the even number field are all indicated by broken lines. Moreover, sampling points in the odd number field and the even number field are indicated by black circles and white circles, respectively.

Here, focusing on the sampling points on the dashed-dotted line M1 that is the scanning center in the main scanning direction, the sampling points in the odd number field and the sampling points in the even number field are arranged at regular intervals D1 in the sub-scanning direction. Also, the sampling points in the two fields are alternately arranged in the sub-scanning direction. On the other hand, focusing on the dashed-dotted lines M2 and M3 away from the center in the main scanning direction of the resonant scanner 3, it can be seen that the sampling points are not arranged at regular intervals in the sub-scanning direction but arranged at intervals D1 to D6. Furthermore, comparison between the relationship among the intervals D1, D2, and D3 on the dashed-dotted line M2 and the relationship among the intervals D4, D5, and D6 on the dashed-dotted line M3 shows that the farther away from the center in the main scanning direction, the less regular the intervals in the sub-scanning direction. Note that, here, the non-regular intervals mean that there are multiple kinds (three kinds in this embodiment) of intervals between the sampling points. Meanwhile, the less regular intervals mean that differences between the multiple kinds of intervals are increased.

Here, considering the relationship between the sampling points and the pixels displayed on the display unit 102 shown in FIG. 6, data of the corresponding pixels is properly acquired from the sampling points on the dashed-dotted line M1. However, as the trajectories get farther away from the center in the main scanning direction, deviation between the data acquisition positions and the pixel arrangement is increased on the dashed-dotted line M2. Furthermore, on the dashed-dotted line M3, the data acquisition positions and the pixel arrangement are not only deviated, but as can be seen from the arrangement of the sampling points that form the interval D5, the data acquisition positions in the sub-scanning direction are switched between the first field and the second field. This results in a region where the actual sampling points and the arrangement of the corresponding pixels are changed. In other words, the sampling points in the first field and the sampling points in the second field, which are alternately arranged in the sub-scanning direction, are no longer alternately arranged.

As described above, the fact that the sampling points are no longer arranged at regular intervals in the sub-scanning direction or cannot be alternately obtained from the two fields means that the SLO image is distorted in the sub-scanning direction. More specifically, an SLO image obtained when the offset amount in the sub-scanning direction for the interlaced scanning is given as shown in FIG. 7 is less and less distorted in the sub-scanning direction as closer to the center in the main scanning direction. On the other hand, the SLO image is distorted in the sub-scanning direction or the generated distortion is increased as farther away from the center in the main scanning direction. However, an attention area desired to be observed in a generated image is positioned in the center of the image in most cases. As for the attention area in the image obtained in such a case, high visibility is achieved.

In the case shown in FIG. 7, the appropriate offset amount of the scanning position in the even number field with respect to the odd number field is the interval D1 on the dashed-dotted line M1. Therefore, the scanning start position of the illumination light in the even number field in this event is set by shifting the scanning start position of the illumination light in the odd number field by the interval D1 as a predetermined amount in the sub-scanning direction. That is, the even number field is set by shifting the scanning start position of the illumination light in the odd number field by the interval D1 in the sub-scanning direction. The interval D1 is actually determined based on the scanning speed in the sub-scanning direction and the period of the resonant scanner 3 (output of the period detecting unit described above). To be more specific, the interval D1 is calculated by multiplying the scanning speed V of the illumination light during the uniform linear motion of the galvano scanner 2 by time that is ¼ of the scanning period T of the illumination light for the resonant scanner 3.

Figure 8:
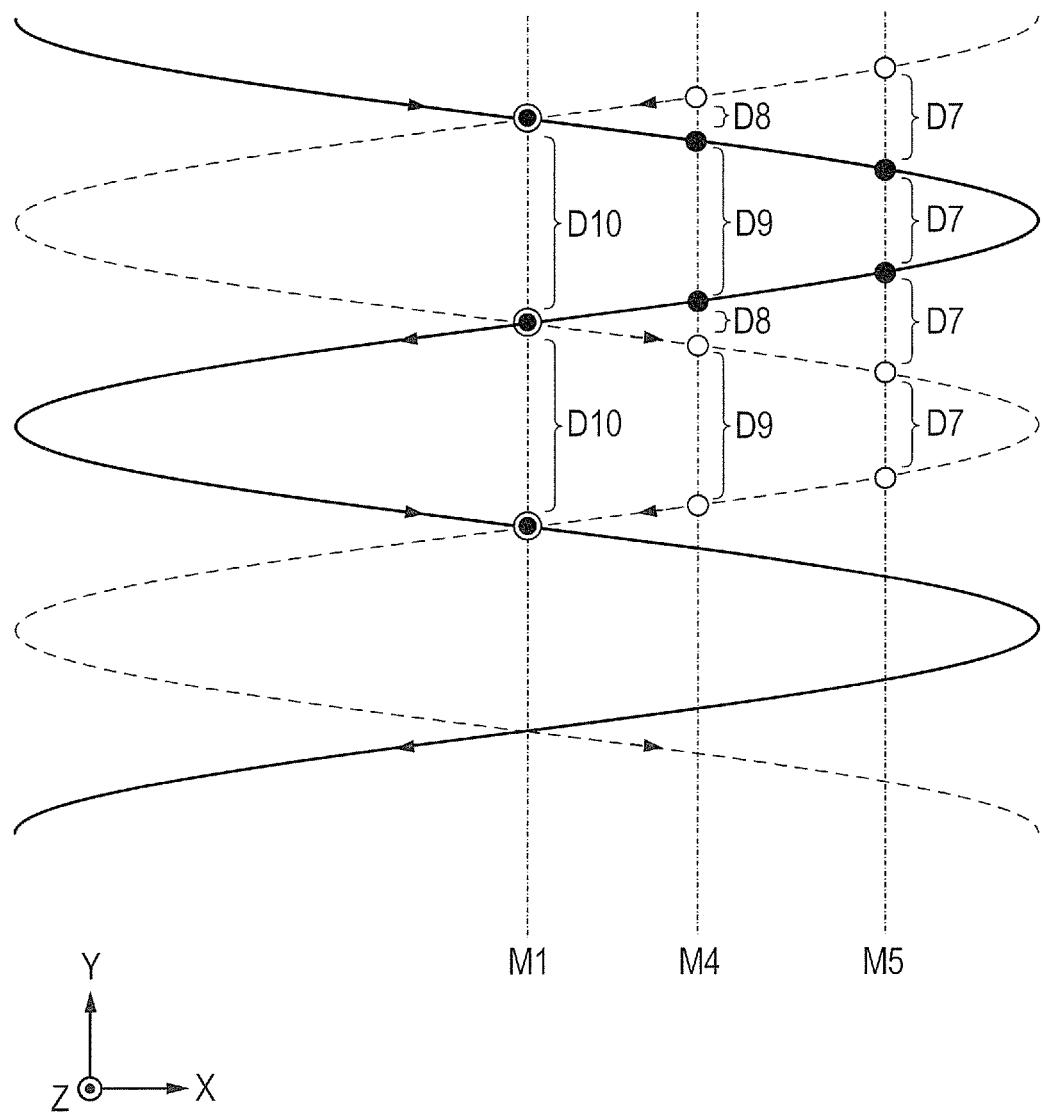
FIG. 8 is a diagram showing a positional relationship between scanning trajectories and sampling points in the two fields when an even number field is generated by being shifted from the odd number field by an inappropriate offset amount.

Next, with reference to FIG. 8, description is given of a case where the even number field is set with an inappropriate shift amount, as a comparison to the example shown in FIG. 7. FIG. 8 shows scanning trajectories and sampling points for both of the odd number field and the even number field in which the offset amount described above is set as an interval D10 for the odd number field.

Here, focusing on the sampling points on the dashed-dotted line M5, the sampling points are arranged at regular intervals D7 in the sub-scanning direction. However, the sampling points in the odd number field and the sampling points in the even number field are arranged so as to be switched at two-point intervals, rather than alternately. Focusing on the sampling points on the dashed-dotted line M4, the sampling points are not arranged at regular intervals but arranged at two kinds of intervals D8 and D9 in the sub-scanning direction. Moreover, in the sub-scanning direction, the sampling points are switched at two-point intervals such that two sampling points in the even number field are arranged after two sampling points in the odd number field. Meanwhile, as for the sampling points on the dashed-dotted line M1, the sampling points in the two fields overlap with each other, and the interval between the overlapping positions is D10. Here, the relationship between the intervals D8 and D9 on the dashed-dotted line M4 is compared with the relationship between the intervals D10 on the dashed-dotted line M1. It can be seen that, as closer to the center in the main scanning direction, the interval D9 becomes closer to the interval D10 and the interval D8 approaches 0, and that the interval between the sampling points arranged in the sub-scanning direction become less regular.

As described above, depending on the offset amount in the sub-scanning direction for the interlaced scanning, distortion generated in the SLO image obtained is increased in the sub-scanning direction as closer to the center in the main scanning direction. Moreover, the distortion is reduced in the sub-scanning direction as farther away from the center in the main scanning direction. Note that the interval D10 that is the offset amount of the scanning position in the even number field with respect to the odd number field in the case of FIG. 8 is calculated by multiplying the scanning speed V during the uniform linear motion of the galvano scanner 2 by time that is ½ of the scanning period T for the resonant scanner 3.

When the shift amount shown in FIG. 7 is the interval D1, the sampling points in the odd number field and the sampling points in the even number field are alternately positioned in the sub-scanning direction on the dashed-dotted line M1, on the dashed-dotted line M2, and in a region outside thereof. Therefore, at the data acquisition positions and the corresponding pixels, arrangement of data acquisition positions and peripheral pixels therearound does not change. Note that, when the shift amount shown in FIG. 8 is the interval D10, all the sampling points in the two fields are positioned at two-point intervals in the sub-scanning direction as described above. In this case, by uniquely setting the sampling points and the pixel arrangement such that the correspondence relationship between the displayed pixels of the SLO image and the sampling points is switched at two-point intervals in the sub-scanning direction, switching of the pixel arrangement can be avoided. However, an area where the SLO image is not distorted is only a peripheral portion of the data acquisition area, which is not appropriate for acquiring information and the like for diagnosis by actually observing the eye fundus and the like.

Thus, in this embodiment, when the even number field is generated with respect to the odd number field, the interval D1 is used as a predetermined amount for shifting the scanning start position of the even number field in the sub-scanning direction. Note that the predetermined amount does not strictly have to be D1, but may be determined for the 2D scans with the illumination light such that the intervals between the odd number field and the even number field in the sub-scanning direction become more regular as closer to the scanning center in the main scanning direction within the data acquisition area. Thus, an SLO image with less distortion in the center or the scanning center in the main scanning direction or the peripheral area thereof is obtained.

Note that it can also be said that an image obtained from the data acquisition area for the purpose of observing a lesion or the like during actual observation of the eye fundus or the like may be less distorted in the attention area. In this case, in the attention area within the data acquisition area, if the sampling points in the two fields are arranged at regular intervals in the sub-scanning direction at the center in the main scanning direction within the area, distortion of the SLO image in the attention area can be suppressed. In this case, two sampling points in the odd number field and two sampling points in the even number field are actually alternately arranged at regular intervals in the sub-scanning direction at the center in the main scanning direction.

For example, it is assumed that the shift amount is set such that some of the sampling points satisfy the conditions described above on the dashed-dotted line M2. Note that, in the following description, the sampling points in the odd number field are referred to as black circles, and the sampling points in the even number field are referred to as white circles. In this case, sets of black and white circles are arranged at constant intervals on the dashed-dotted line M2, each set including the black circle, white circle, black circle, and white circle arranged in descending order at regular intervals. The constant interval between the white circle at the bottom of the set and the black circle at the top of the next set is larger than the regular interval described above. As the shift amount between the even number field and the odd number field illustrated in FIG. 7 is reduced, the position of one set in the sub-scanning direction, the set including the black circle, white circle, black circle, and white circle arranged at regular intervals, is shifted from the dashed-dotted line M1 to the dashed-dotted line M3. Moreover, as the position of the set is shifted, the interval between the upper set and the lower set is increased. Meanwhile, when the shift amount exceeds D1, the area in the main scanning direction where the arrangement order changes is increased. As a result, the regular interval in the arrangement order described above cannot be maintained.

That is, the shift amount is preferably not more than D1. Thus, among the sampling point in the odd number field, the sampling point in the even number field, the sampling point in the odd number field, and the sampling point in the even number field, which are arranged in the sub-scanning direction, the alternate arrangement with the regular interval is partially maintained. Note that this condition is for the area in a separating direction from the scanning center (M1) in the main scanning direction during the forward scanning. The condition is reversed for a region in an approaching direction to the scanning center (M1) in the main scanning direction during the forward scanning.

Therefore, despite partial distortion, the condition of the alternate arrangement with the regular interval is satisfied for at least four sampling points. Thus, a certain degree of distortion in the SLG image can be suppressed.

Moreover, the pixel arrangement corresponding to the sampling points during the data acquisition needs to be changed depending on whether the sampling points in the sub-scanning direction are arranged alternately or at two-point intervals between the two fields, for example, as described with reference to FIG. 8. However, if an area where the arrangement of the sampling points is constant exceeds a range where a certain area is the attention area, the pixel arrangement no longer needs to be accordingly changed. This leads to reduction in computational load during image generation. Here, as for the eye fundus image, basically the central region of the data acquisition area is often used as the attention area. That is, an ideal position of the attention area is the center of the data acquisition area, and the center of the attention area in the main scanning direction in this case is the scanning center in the main scanning direction. Therefore, as for the interval D1 that is the offset amount, at as preferable that the condition shown in FIG. 7 is used as a base and a condition that the attention area is moved to a peripheral area from the base condition and the sampling points are alternately arranged at regular intervals as described above at the center of the attention area in the main scanning direction is satisfied.

After setting the even number field with the offset amount obtained based on the reason described above, the controller 10 performs a 2D scan with the illumination light for the even number field in Step S207. After the acquisition of data by the 2D scan, the image generator 11 generates in Step S208 an SLO image of the even number field from the 2D scan data acquired in Step S207. The generated SLO image is displayed on the display unit 102 or the displayed SLO image is updated to the newly generated SLO image.

An SLO moving image is acquired during alignment in the eye fundus observation, and an SLO still image is acquired during shooting. Therefore, as for the SLO moving image during alignment, the operations from Step S201 to Step S208 may be repeated. Meanwhile, as for the SLO still image during shooting, one still image may be generated from the data of the odd number field and the even number field acquired in Steps S205 and S208.

As described above, by shifting the scanning position of the even number field from the odd number field by the interval D1 that is the predetermined amount, distortion of the SLO image about the main scanning direction can be prevented when the SLO image is seen on the pixels in the sub-scanning direction. At the ophthalmic clinic, the attention area such as a diseased area of the eye to be inspected, which is desired to be acquired, often positioned in the center of the image. Thus, an SLO image suitable for diagnosis and the like can be provided. Moreover, as for the scanning with the illumination light, since image acquisition is performed by the reciprocating scanning and the interlaced scanning, a higher resolution and a higher frame rate can be achieved at the same time by the combination thereof.

Figure 9:
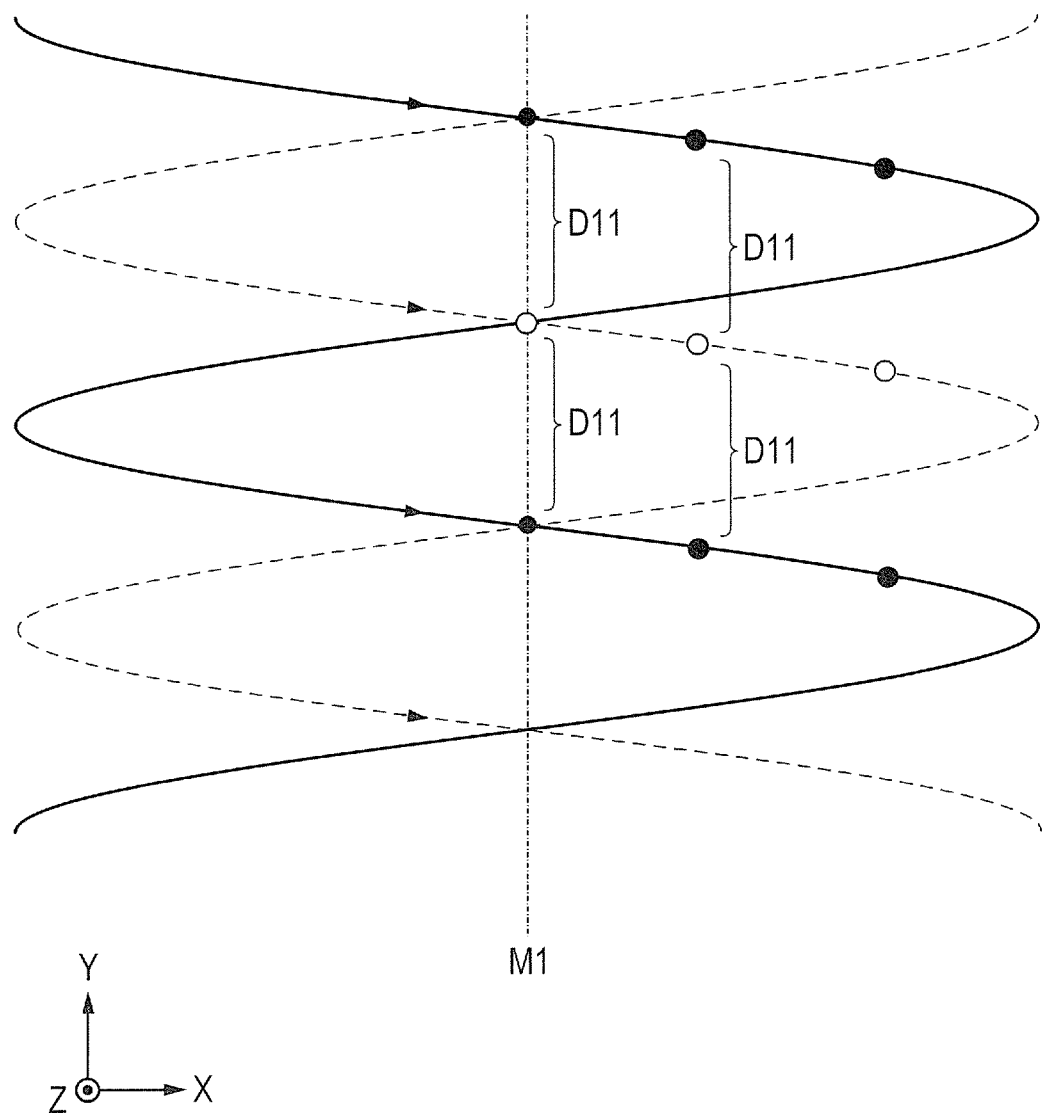
FIG. 9 is a diagram illustrating scanning trajectories and sampling points when sampling is performed under a condition that one-side scanning is performed simultaneously with interlaced scanning with the illumination light.

Here, the setting of the even number field by the offsetting by the predetermined amount is effective only in the case of the reciprocating scanning performed simultaneously with the interlaced scanning, and is ineffective in the case of one-side scanning performed simultaneously with the interlaced scanning. FIG. 9 shows scanning trajectories of the measurement light and sampling points in the case of the one-side scanning performed simultaneously with the interlaced scanning. In this case, with the interval D11 used as the offset amount, the SLO image is not distorted in the sub-scanning direction. However, the amount of pixel data acquired is reduced, making it difficult to improve the resolution. Note that the one-side scanning means sampling performed only in either one of forward scanning and backward scanning.

While the even number field is offset to the lower side of the page space of FIG. 7 from the odd number field in the embodiment described above, the same effect can also be achieved by offsetting the even number field to the upper side of the page space. Moreover, the number of the fields is not limited to two, i.e., the odd number field and the even number field, but more fields may be provided as described above. Thus, in this embodiment, the odd number field is defined as the first field, and the even number field is defined as the second field different from the first field.

Note that, in the above embodiment, the description is given of the SLO using the resonant scanner and the galvano scanner 2 for scanning with the illumination light, as an example. In the embodiment, the resonant scanner 3 constitutes a first scanning member that performs reciprocating scanning of the eye to be inspected in the main scanning direction with the illumination light. Meanwhile, the galvano scanner 2 constitutes a second scanning member that scans the eye to be inspected at a constant speed with the illumination light in the sub-scanning direction that intersects with the main scanning direction. The main scanning direction and the sub-scanning direction are preferably perpendicular to each other as in the case of the embodiment, but may also be set to intersect with each other at a certain angle. The controller 10 as a scanning control unit allows both the scanners described above to perform a 2D scan of the eye to be inspected with the illumination light in the odd number field within the data acquisition area, and also to perform a 2D scan thereof in the even number field different from, the odd number field within the data acquisition area. The photodiode 7 and a module in the controller 10 that allows the photodiode to acquire data such as luminance at the timing described above constitute a data acquisition unit. The image generator 11 as an image generation unit generates an SLO image from data acquired based on the illumination light returned from the eye to be inspected in the odd number field and the even number field.

As described above, the controller 10 obtains the predetermined amount as the offset amount based on the scanning speed during the uniform linear scanning with the illumination light by the galvano scanner 2 and the output from the period detecting unit. Furthermore, the controller 10 determines the timing to acquire data, based on the output from the period detecting unit and an output from the amplitude detecting unit, such that the data acquired from the odd number field and the data acquired from the even number field are arranged in a straight line in the sub-scanning direction.

Note that, in the above embodiment, the description is given of the example of using the resonant scanner in the main scanning direction. Alternatively, the present invention is also applicable to a case of using the galvano scanner that accelerates and decelerates during the scanning with the illumination light, an acousto-optic deflector or a micro electro mechanical system (MEMS) scanner in the main scanning direction. Moreover, in the above embodiment, the scanning with the illumination light in the main scanning direction is performed by the scanning unit that accelerates and decelerates, while the scanning with the illumination light in the sub-scanning direction is performed by the scanning unit that performs uniform linear motion. However, the same effect can be achieved with a configuration in which these scanning units are switched to perform scanning by the uniform linear motion in the main scanning direction and scanning that accelerates and decelerates in the sub-scanning direction.

(Embodiment 2)

Next, an inspection apparatus according to Embodiment 2 of the present invention is described. Note that, since the configuration of the SLO, scanning of a correction photodiode with illumination light, an output signal from the correction photodiode, relationships between scanning directions and positions are described in Embodiment 1, description thereof is omitted here.

Figure 10:
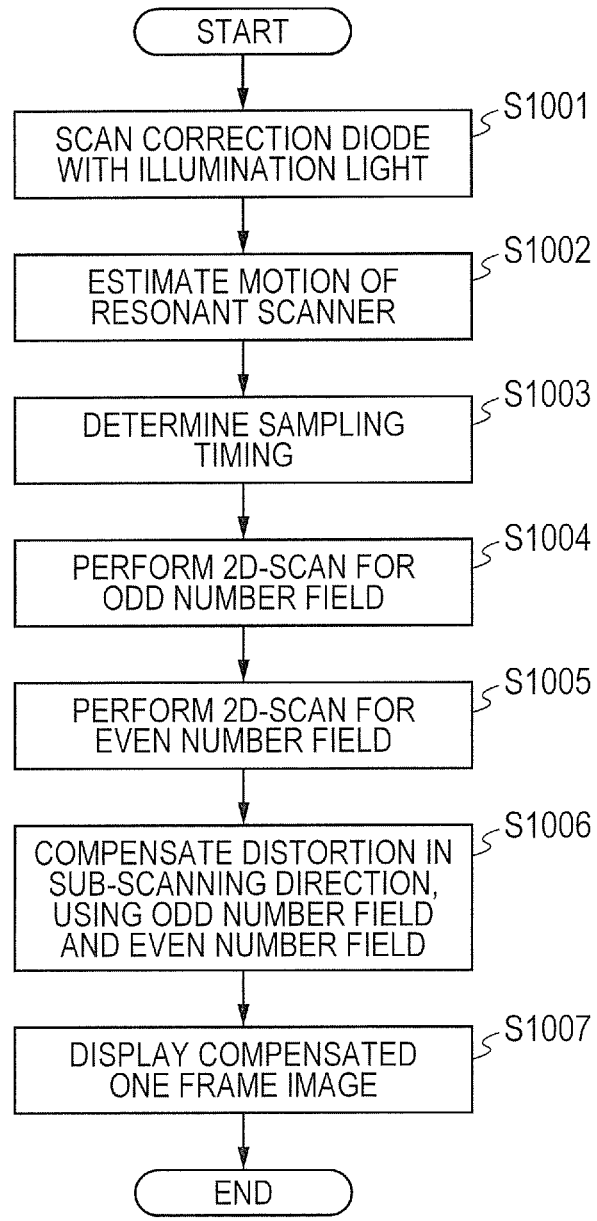
FIG. 10 is a flowchart showing an image acquisition flow according to Embodiment 2 of the present invention.

Hereinafter, with reference to a flowchart of FIG. 10, description is given of a flow of steps executed during image acquisition by the SLO including the data acquisition unit 100, the system unit 101, and the display unit 102 described above in Embodiment 2. Also, the respective steps are accordingly described in detail with reference to FIGS. 3, 4A, 4B, 11, and 12. The flowchart constitutes one aspect of a method for controlling the inspection apparatus according to Embodiment 2, and respective steps of the flowchart constitute respective steps of the method. Note that, in the flowchart, processing performed in Steps S1001 and S1002 is the same as the processing performed in Steps S201 and S202 in Embodiment 1. In Step S1003, the controller 10 determines timing of data sampling in the odd number field and the even number field performed in subsequent Steps S1004 and S1005, as in the case of Step S203. In this event, intersection positions shown in FIG. 12 to be described later are further obtained based on the estimated motion of the resonant scanner 3, as data acquisition positions on the eye fundus.

Note that, in this embodiment, a scanning optical system using the resonant scanner improves the resolution by performing reciprocating scanning to acquire information. On the other hand, a higher frame rate can, be achieved by performing interlaced scanning with the illumination light to acquire images in the odd number field and the even number field, respectively. In the embodiment described below, a higher resolution as well as a higher frame rate is achieved and a less distorted high-resolution image is provided by performing the interlaced scanning and the reciprocating scanning in combination.

In this embodiment, a one frame image is generated from data acquired by combining data acquired from the odd number field and the even number field. Thus, in the following embodiment, images are generated and updated by acquiring data from two different fields on the eye fundus through interlaced scanning with illumination light. Moreover, a higher frame rate is achieved by simultaneously acquiring data from both of forward scanning and backward scanning during the scanning with the illumination light. To be more specific, in the technology disclosed in Japanese Patent Application Laid-Open No. 2014-68703 described above, data of all lines within a data acquisition area is acquired by reciprocating scanning. On the other hand, in this embodiment, data of all lines is acquired by performing reciprocating scanning of an odd number frame and reciprocating scanning of an even number frame.

Figure 11:
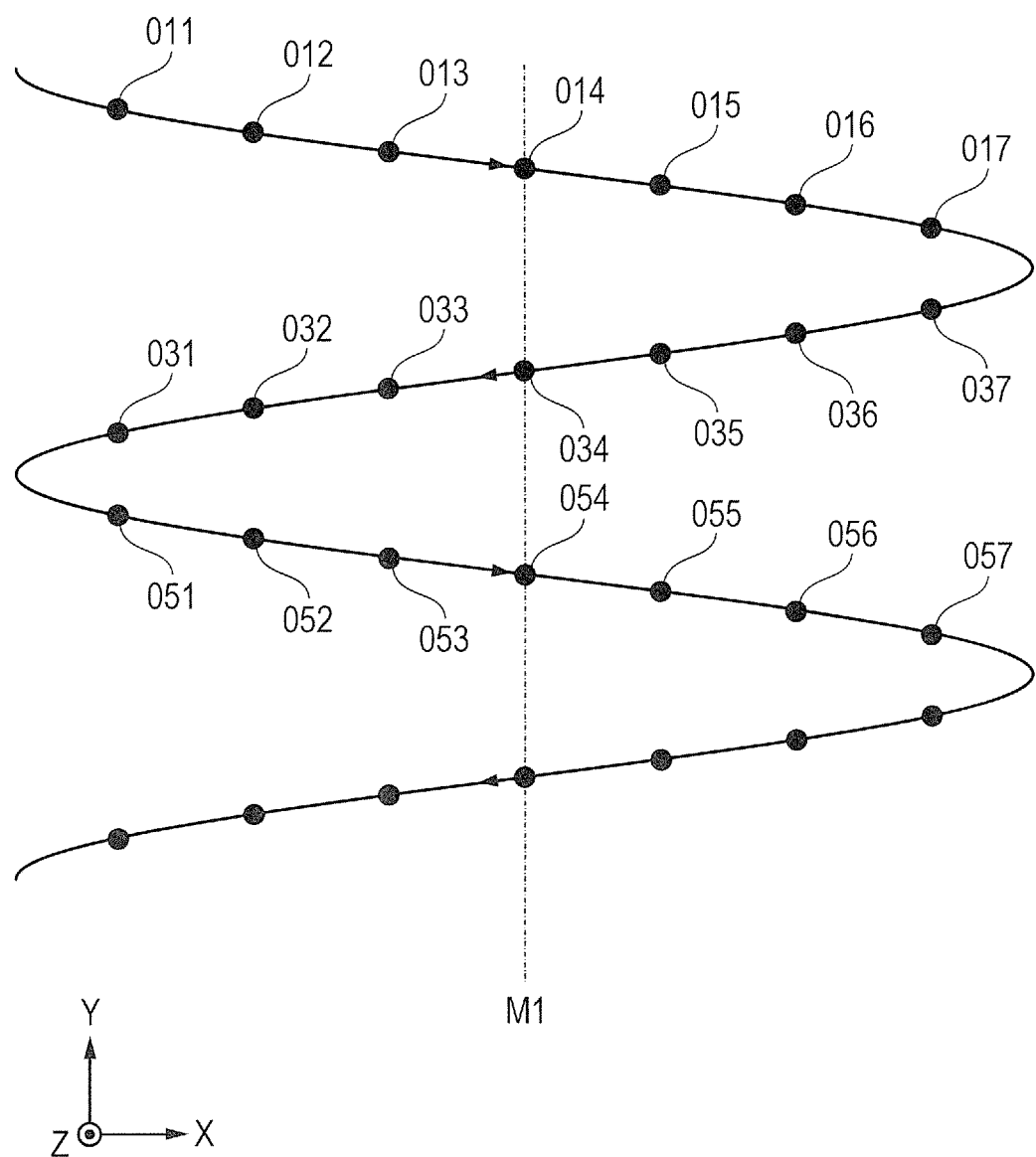
FIG. 11 is a diagram illustrating a scanning trajectory and sampling points in an odd number field.

Hereinafter, as for image display processing to be performed in this embodiment, processing different from that in Embodiment 1 is described. FIG. 11 illustrates a scanning trajectory and sampling points in scanning with the illumination light in the odd number field, which is performed in Step S1004. In FIG. 11, the scanning trajectory is drawn with a solid line, and the sampling points are represented by black circles. In FIG. 11, the scanning trajectory indicated by the right-pointing arrow extends from the part to the left of a sampling point O11 to the part to the right of a sampling point O17. Meanwhile, the scanning trajectory indicated by the left-pointing arrow extends from the part to the right of a sampling point O37 to the part to the left of a sampling point O31. The directions of the arrows in FIG. 11 show that forward scanning and backward scanning by the resonant scanner 3 are switched at the right and left ends of the scanning trajectory. Note that the points indicated by black circles in FIG. 11 represent sampling points in the odd number field within the data acquisition area on the eye fundus Er. In FIG. 11, as described above, the presence of the black circles in both of the forward scanning and the backward scanning during the reciprocating scanning shows that the data acquisition is carried out in both of the forward scanning and the backward scanning by the resonant scanner 3. Note that the dashed-dotted line M1 in FIG. 11 represents the center in the main scanning direction in the main scanning area of the illumination light by the resonant scanner 3.

All the sampling points acquired in the odd number field are sampled at regular intervals in the main scanning direction. This is because the sampling timing is calculated in Step S1003 such that the desired sampling points can be obtained, and then the sampling is performed based on the calculation. However, the sampling points are not arranged at regular intervals in the sub-scanning direction. This is because the motion of the resonant scanner 3 changes with time in the sinusoidal pattern shown in FIGS. 4A and 4B.

In subsequent Step S1005, the controller 10 performs scanning in the even number field during the interlaced scanning of the eye fundus Er. In this event, the controller 10 shifts the scanning position in the even number field from the odd number field by a predetermined amount in the sub-scanning direction such that the scanning position in the odd number field and the scanning position in the even number field do not overlap with each other. Note that the predetermined amount in this embodiment corresponds to the interval between rows of pixels in the sub-scanning direction in the image displayed on the display unit 102, and is approximately equal to the interval between the sampling points in the odd number field and the even number field, which are alternately arranged on the sub-scanning line in the center of the main scanning area.

Figure 12:
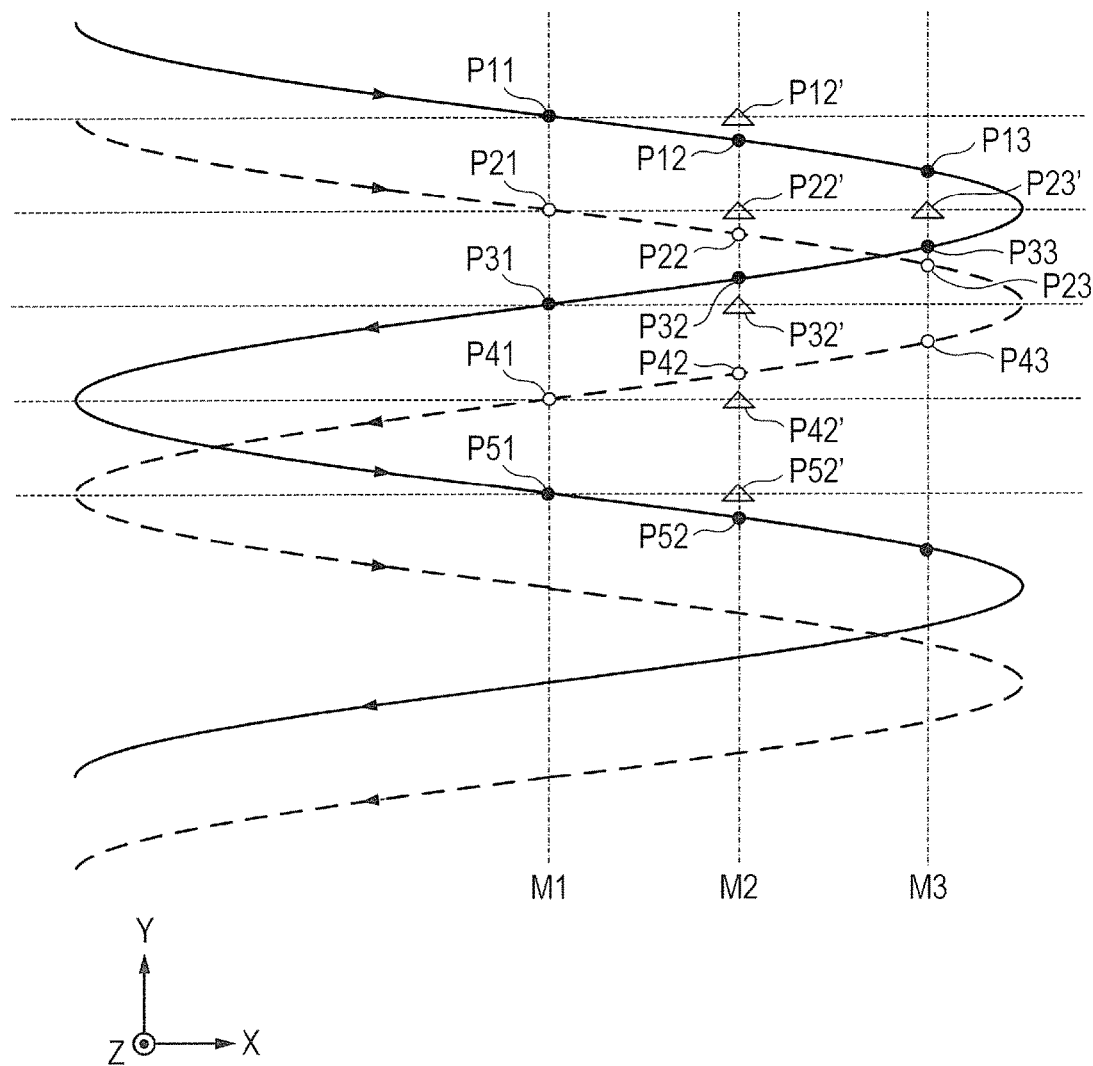
FIG. 12 is a diagram showing a positional relationship between desired sampling points for compensating image distortion in the sub-scanning direction and scanning trajectories and sampling points in the odd number field and the even number field.

FIG. 12 shows scanning trajectories and sampling points in the odd number field and the even number field scanned in Steps S1004 and S1005. In FIG. 12, the scanning trajectory in the odd number field is indicated by a solid line, which is the trajectory of the scanning with the illumination light performed in Step S1004. Meanwhile, the scanning trajectory in the even number field is indicated by a broken line, which is the trajectory of the scanning with the illumination light performed in Step S1005. Also, the sampling points in the odd number field and the even number field are indicated by black circles and white circles, respectively. To be more specific, in FIG. 12, the black circles P11, P12, P13, P33, P32, P31, P51, P52, . . . represent the sampling points in the odd number field. Meanwhile, the white circles P21, P22, P23, P43, P42, P41, . . . represent the sampling points in the even number field.

Here, focusing on the sampling points on the dashed-dotted line M1 positioned at the center in the main scanning direction shown in FIG. 12, the sampling points in the odd number field and the sampling points in the even number field are arranged at regular intervals in the sub-scanning direction. To be more specific, the intervals between the sampling points indicated by the black circle P11, the white circle P21, the black circle P31, the white circle P41, and the black circle P51 are all equal distances. By setting a proper value for a predetermined offset amount as described above, the sampling points on the eye fundus and the pixels on the display screen corresponding to the sampling points can correspond to each other without being deviated from each other. This can prevent image distortion in the sub-scanning direction at the center in the main scanning direction.

On the other hand, focusing on the dashed-dotted lines M2 and M3 away from the center in the main scanning direction, it can be seen that the sampling points are not arranged at regular intervals in the sub-scanning direction. To be more specific, the intervals between the sampling points indicated by the black circle P12, the white circle P22, the black circle P32, the white circle P42, and the black circle P52 are not regular but different from each other. The fact that the sampling points are not arranged at regular intervals in the sub-scanning direction means that the SLO image is distorted in the sub-scanning direction. Moreover, with reference to FIG. 12, it is assumed that the farther away from the center in the main scanning direction, the less regular the sampling intervals in the sub-scanning direction, and that the image distortion in the sub-scanning direction is also increased. Note that, here, the non-regular intervals mean that there are multiple kinds (three kinds in this embodiment) of intervals between the sampling points. Meanwhile, the less regular intervals mean that differences between the multiple kinds of intervals are increased.

In Step S1006, the image generator 11 generates a one frame image by compensating the distortion in the sub-scanning direction generated in Steps S1004 and S1005 described above. In this embodiment, the distortion in the sub-scanning direction occurs on the dashed-dotted lines M2 and M3 rather than on the dashed-dotted line M1, as described above. Therefore, the compensation of the distortion in the sub-scanning direction performed in this Step S1006 is executed for the data sampled on the dashed-dotted lines M2 and M3. Note that the sampled data is used to generate an SLO image, as pixel values such as luminance values of the corresponding pixels. For the compensation, such data is also obtained as the pixel values. Therefore, in the following description, the data acquired by the compensation is described as the pixel value.

Here, as described above, as for the sampling points on the dashed-dotted line M1, data can be acquired corresponding to the pixels on the display screen without any positional deviation. FIG. 12 also shows the dotted lines perpendicular to the dashed-dotted line M1 through the sampling points on the dashed-dotted line M1 as well as the positions where the dotted lines intersect with the dashed-dotted lines M2 and M3, respectively. As for all of such intersection positions, there are positionally corresponding pixels on the display screen. Therefore, the compensation of the distortion in the sub-scanning direction is performed by estimating pixel values at the intersection positions arranged at regular intervals in the sub-scanning direction from the actually acquired data of the sampling points. In this embodiment, as for the dashed-dotted line M2, pixel values at intersection positions P12', P22', P32', P42', and P52' are estimated from the actually acquired data of the sampling points indicated by the black circle P12, the white circle P22, the black circle P32, the white circle P42, and the black circle P52. Note that it is preferable that the image generator 11 previously sets such intersection positions as new positions to generate data for compensating the image distortion.

Hereinafter, as a specific example, description is given of estimation of a pixel value at the intersection position P22' on the dashed-dotted line M2. The estimation of the pixel value is performed using a first degree equation expressed by Equation (2). In Equation (2), Py represents a coordinate position (coordinate position on the dashed-dotted line M2) of the sampling point in the sub-scanning direction, E represents a pixel value at Py, and C and D represent coefficients.

[Equation 2]

$$E = C \cdot Py + D \tag{2}$$

Among the actually acquired sampling data, data of two sampling points located closest to the intersection position P22' is selected and plugged into Equation (2).

Note that, in this event, these two sampling points are selected irrespective of the field from the odd number field and the even number field, where the fields for acquiring the data are continuously provided in chronological order.

Then, distances between the intersection positions indicated by white triangles in FIG. 12 for estimating the pixel values or data and all the sampling points, which indicated by black circles and white circles in FIG. 12 and previously set, on the same sub-scanning line are obtained. Thereafter, data of the sampling points with the shortest distance by comparing the distances thus obtained and data of the sampling points with the second shortest distance are selected as data used to compensate the distortion. Note that, although the data of the two sampling points from the shorter distance side in the embodiment described here, data of three or more sampling points may be used. However, depending on the value of the offset amount, it is also conceivable that the second or third data is too distant from the intersection positions for use in compensating the distortion. In this case, a distance threshold may be provided to select data of the sampling points at a distance within the threshold from the intersection positions for estimating the pixel values or data.

As described above, if the two sampling points are both in the odd number field, the two sampling points may be both selected from the odd number field. Alternatively, if the two sampling points are in the two fields, one in the odd number field and the other one in the even number field, the two sampling points may be selected from the two fields, respectively. Normally, the data compensation in the interlaced scanning is performed for each field, and candidates for data to be used for the compensation are selected within the field. On the other hand, in this embodiment, data candidates for use in estimating pixel values are used for all the data acquired in chronologically continuous multiple (two in this embodiment) fields set to generate one image.

To be more specific, taking the intersection position P22' as an example, two sampling points closer to the intersection position P22' are the black circle P12 and the white circle P22. Therefore, coordinate positions and pixel values of the black circle P12 and the white circle P22 in the sub-scanning direction are (Py12, E12) and (Py22, E22), respectively, which are plugged in for (Py, E) in Equation (2). The constants C and can be obtained from the two equations thus obtained. The coordinate positions of the sampling points actually acquired here are calculated by the controller 10. The controller 10 calculates the coordinate positions based on the motion of the resonant scanner 3 estimated in Step S1002, the sampling timing obtained in Step S1003, and the relationship of speed of the galvano scanner 2.

Next, the obtained constants C and D are used and the coordinate position Py22' of the intersection position P22' in the sub-scanning direction, which is a desired sampling point, is plugged in for Py in Equation (2). Then, a pixel value P22' of the desired sampling point can be estimated. Thus, the data of the sampling point closest to the desired sampling point can be selected irrespective of the odd number field or the even number field. Therefore, the accuracy of the estimation of the pixel values within the display screen described above can be improved.

Meanwhile, as described above, the image distortion in the sub-scanning direction generally compensated for each field. Accordingly, in order to acquire compensated data, two points closest to a position to generate the data in the field have to be selected from among sampling points included in the field. Therefore, there is also a case where distant points have to be selected compared with the case of this embodiment described above. For example, in the case of estimating the pixel value of the intersection position P22' in the odd number field shown in FIG. 12, data of two sampling points indicated by the black circles P12 and P32 in the odd number field is selected. As a result, the accuracy of the estimation of the pixel value is reduced, leading to image distortion and blurring.

Note that, in the above example, the combination of the sampling points indicated by the black circle P12 and the white circle P22 is selected. However, even when a combination of the sampling points indicated by the white circle P22 and the black circle P32 is selected, the sum of distances between the intersection position P22' and these two points is equal to or close to the sum of the distances in the case of the combination of the black circle P12 and the white circle P22. Alternatively, the distance between the intersection position P22' and the black circle P12 is equal to or close to the distance between the intersection position P22' and the black circle P32. Therefore, even when such sampling points are selected, the effect that the pixel value can be estimated with equally good accuracy can be achieved.

The method for estimating the pixel value of the intersection position P22' described above is also applied to all the other desired intersection positions to estimate pixel values at the respective intersection positions. For example, the pixel value at the intersection position P23' is estimated using data of the sampling points indicated by the black circles P13 and P33. The pixel value at the intersection position P32' is estimated using data of the sampling points indicated by the black circle P32 and the white circle P42 or data of those indicated by the white circle P22 and the black circle P32. More specifically, pixel values at all the intersection positions within the one frame image are generated from both the odd number field and the even number field. Note that, in this embodiment, there is no need to estimate pixel values at the intersection positions on the dashed-dotted line M1. However, depending on the offset amount for generating the even number field, the same processing is required for those on the dashed-dotted line M1.

Next, in Step S1007, the controller 10 displays the image generated from the pixel values estimated in Step S1006 on the display unit 102. Note that, in this embodiment, replacement of a frame to be generated from the sampling points in the odd number field and the even number field with a frame including intersection positions and setting pixel values of the intersection positions to be the estimated pixel values are referred to as compensation of distortion. In this embodiment, as a result of compensating the distortion of the SLO image in the sub-scanning direction by the image generator 11 in Step S1006, the distortion of the one frame image is compensated using all the data in both of the odd number field and the even number field. Therefore, the image generated in Step S1007 and displayed on the display unit 102 is in a unit of one frame rather than one field.

As described above, in this embodiment, an image without distortion in the sub-scanning direction is generated by using the scanning optical system including the resonant scanner 3 and the galvano scanner 2 to acquire data from the two fields by the reciprocating scanning and the interlaced scanning with the illumination light. To be more specific, data of sampling points at multiple positions closer to a desired sampling point (referred to as the intersection position in this embodiment) where a pixel value is to be obtained is used irrespective of the odd number field and the even number field to estimate the pixel value of the desired sampling point. By generating an image with the estimated pixel value, a one frame image can be provided, in which distortion in the sub-scanning direction is compensated with high accuracy.

For example, the technology disclosed in Japanese Patent Application Laid-Open No. 2014-68703 described above is intended to cope with the distortion of the image in the sub-scanning direction, which is generated by the reciprocating scanning with the illumination light by using the resonant scanner. However, the disclosed configuration compensates the distortion every time one frame is obtained in the case of the reciprocating scanning and progressive scanning with the illumination light. Thus, if the method disclosed in this embodiment wherein the reciprocating scanning and the interlaced scanning are performed is applied, the processing of compensating the distortion is executed for each field. As described above, in the method disclosed in Japanese Patent Application Laid-Open No. 2014-68703 described above, a pixel value of a desired sampling point is estimated by using data of sampling points at an equal distance in the sub-scanning direction from a desired sampling position. Moreover, an image having distortion compensated is obtained from a field including the estimated pixel value. Therefore, the above method includes a case where the sampling points in the data to be used are away from the desired sampling point. In this case, the image having the distortion compensated is blurred in the sub-scanning direction. Here, a case is considered, for example, where the above processing is performed in each of the odd number field and the even number field and then a new one frame image is generated from these fields as in the case of this embodiment. In this case, blurred portions overlap with each other, and thus the blurring is further increased. Such image blurring can be avoided by appropriately selecting data of the odd number field and the even number field to obtain the pixel value and then generating a one frame image from the two fields as described above.

Note that, although the first degree equation as shown in Equation (2) is used to estimate the pixel value in Embodiment 2 described above, an N-th degree equation such as a third degree equation and a fifth degree equation may be used. In this event, the same effect can be achieved by selecting N+1 sampling points located closest to each of desired sampling points arranged at regular intervals in the sub-scanning direction, irrespective of the odd number field and the even number field.

Moreover, in this embodiment, the data acquisition from the even number field is performed after the data acquisition from the odd number field, and then the data of these two fields is used to generate an image having distortion compensated. However, the order of the data acquisition is not limited thereto but may be switched. That is, the same effect can be achieved by using data of different fields acquired continuously in chronological order to generate a one frame image. Furthermore, in this embodiment, the even number field is generated by offsetting the odd number field to the lower side of the page space of FIG. 12. However, the same effect can be achieved by offsetting to the upper side of the page space to generate the even number field. Moreover, the number of the fields is not limited to two, which is defined by the odd number and the even number, but more fields may be provided. Thus, in this embodiment, the odd number field corresponds to the first field, and the even number field corresponds to the second field different from the first field.

(Embodiment 3)

Figure 13:
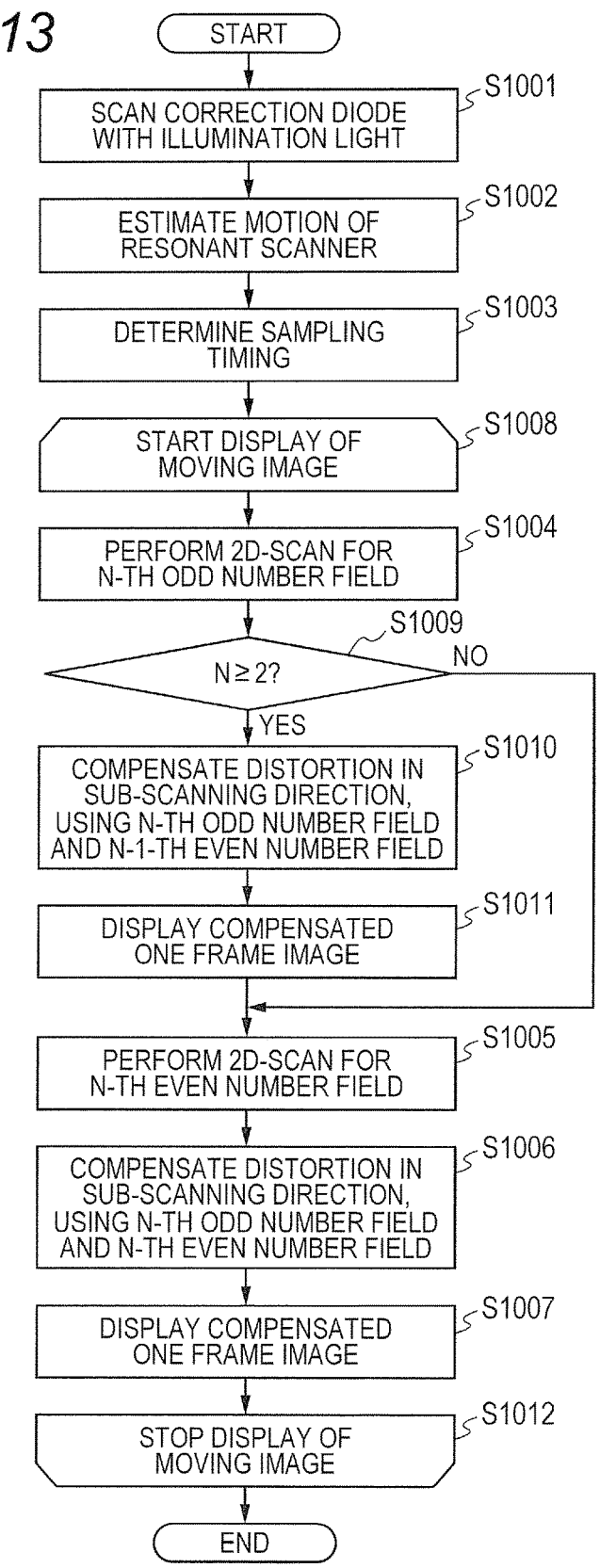
FIG. 13 is a flowchart showing a flow of acquiring a moving image according to Embodiment 3 of the present invention.

In Embodiment 2 described above, the description is given of the case of generating a one frame still image. On the other hand, Embodiment 3 described below is intended to generate a moving image. Note that an SLO according to Embodiment 3 has the same configuration as that in Embodiments 1 and 2 shown in FIG. 1. Therefore, Embodiment 3 is described below with reference to a flowchart of FIG. 13 showing a different processing flow from that in Embodiment 2. In the flowchart of FIG. 13, steps for performing the same processing as that executed in Embodiment 2 are denoted by the same step numbers.

In Embodiment 2, the description is given up to the generation of a one frame image having compensated distortion in the sub-scanning direction by using the odd number field and the even number field. Embodiment 3 is intended to continuously generate such images as a moving image and to display the moving image. To be more specific, in the flowchart shown in FIG. 13, the controller 10 first performs a series of operations from Step S1001 to Step S1012. Then, the operations by the controller 10 and the like, such as the data acquisition from the odd number field, the data acquisition from the even number field, and the image generation, in Steps S1008 to S1012 are repeated. Note that N represents the number of repetitions in the flowchart of FIG. 13. The moving image described in Embodiment 3 is mainly used for alignment between the eye to be inspected and the ophthalmic imaging apparatus.

The operations performed in the respective steps are described in detail below. First, when the processing of generating an SLO moving image is started by the controller 10, the flow moves to Step S1001. As in the case of Embodiment 2, the controller 10 estimates motion of the resonant scanner 3 by using data obtained by scanning the correction photodiode 9 with the illumination light in Steps S1001 and S1002.

In subsequent Step S1003, the controller 10 determines sampling timing in the odd number field and the even number field performed in Steps S1004 and S1005. Once the sampling timing is determined, the flow moves to the operations of Step S1008 that is processing for actually displaying the SLO moving image by the controller 10 to Step S1012. In order to display the SLO moving image, the controller 10 performs in Step S1004 N-th scanning with the illumination light in the odd number field and data acquisition from the odd number field. In subsequent Step S1009, the controller 10 determines whether or not the scanning with the illumination light in the odd number field and the data acquisition performed in Step S1004 are the second time around or more.

When the controller 10 determines in Step S1009 that N is 1, i.e., the first data acquisition is performed, the flow sequentially advances to Step S1005, Step S1006, and then Step S1007. As a result, the image generator 11 uses the data acquired from the odd number field in the first data acquisition and the data acquired from the even number field in the first data acquisition to generate a one frame image having compensated distortion in the sub-scanning direction. Then, the display unit 102 displays the generated one frame image. The operations executed in the respective steps described above are the same as those described in Embodiment 2.

On the other hand, when it is determined in Step S1009 that N is 2 or more, i.e., the scanning with the illumination light and the data acquisition in the odd number field are the second time around or more, the controller 10 moves the flow to Step S1010. In Step S1010, the image generator 11 uses data acquired from the Nth odd number field and data acquired from the N−1-th even number field to generate an image having compensated distortion in the sub-scanning direction. In this embodiment, if the data is acquired from the odd number field and from the even number field, respectively, the distortion in the sub-scanning direction can be compensated. Therefore, the latest acquired data of the N-th odd number field and the second latest acquired data of the N−1-th even number field are used to generate the image having compensated distortion in the sub-scanning direction. Since the details of the generation of the image having compensated distortion are the same as those in Embodiment 2, description thereof is omitted here.

Next, Step S1011, the one frame image having compensated distortion in the sub-scanning direction in Step S1010 is displayed on the display unit 102 by the controller 10. In the next. Step S1005, scanning with the illumination light and data acquisition in the N-th even number field are performed. Thus, in subsequent Step S1006, the image generator 11 compensates the distortion by using the latest acquired data of the N-th odd number field and the data of the N-th even number field. In subsequent Step S1007, the one frame image having compensated distortion in the sub-scanning direction in Step S1006 is displayed on the display unit 102.

Thereafter, the controller 10 and the like repeat the processing from Step S1008 to Step S1012 until the generation of the SLO moving image is completed in Step S1012. As a result, the moving image having compensated distortion in the sub-scanning direction can be displayed on the display unit 102. By continuously displaying the images obtained according to the operations described above, a moving image having suppressed distortion in the sub-scanning direction can be provided with a high frame rate.

Note that, in Embodiments 2 and 3 described above, the description is given of, as an example, the SLO using the resonant scanner 3 and the galvano scanner 2 for the scanning with the illumination light. In this example, the resonant scanner 3 constitutes a first scanning member that performs reciprocating scanning of the eye to be inspected in the main scanning direction with the illumination light. Meanwhile, the galvano scanner 2 constitutes a second scanning member that scans the eye to be inspected at a constant speed with the illumination light in the sub-scanning direction that intersects with the main scanning direction. The main scanning direction and the sub-scanning direction are preferably perpendicular to each other as in the case of the embodiments, but may also be set to intersect with each other at a certain angle. The controller 10 as a scanning control unit allows both the scanners described above to perform a 2D scan of the eye to be inspected with the illumination light in the odd number field within the data acquisition area, and also to perform a 2D scan thereof in the even number field different from the odd number field within the data acquisition area. The photodiode 7 and a module in the controller 10 that allows the photodiode to acquire data such as luminance at the timing described above constitute a data acquisition unit. The controller 10 further constitutes an acquisition position setting unit that sets a data acquisition position for acquiring data from the illumination light returned from the eye to be inspected in, the odd number field and the even number field.

Meanwhile, the image generator 11 constitutes a generation position setting unit that previously sets a data generation position to be a desired sampling point. To be more specific, the image generator 11 sets data generation positions for generating an image, which are arranged at first intervals in the main scanning direction and at second intervals in the sub-scanning direction. In the embodiments described above, the first predetermined intervals correspond to the intervals between the sampling points determined in Step S203. However, if the predetermined intervals are regular intervals, the present invention is not limited thereto. Meanwhile, the second intervals between the data generation positions are set to be regular intervals in the sub-scanning direction. The image generator 11 further constitutes a selecting unit that selects data acquired at least at two positions located closest to each of the data generation positions, among the data acquisition positions set in the chronologically continuous odd number field and even number field. The image generator 11 generates data of the data generation positions from the selected data, and then generates an image of the object to be inspected based on the generated data, as an image generation unit.

As described above, the controller 10 obtains the predetermined amount as the offset amount based on the scanning speed during the uniform linear scanning with the illumination light by the galvano scanner 2 and the output from the period detecting unit. Furthermore, the controller 10 determines the timing to acquire data based on the output from the period detecting unit and an output from the amplitude detecting unit, such that the data acquired from the odd number field and the data acquired from the even number field are arranged in a straight line in the sub-scanning direction.

Note that, in Embodiments 2 and 3 described above, the description is given of the example of using the resonant scanner in the main scanning direction. Alternatively, the present invention is also applicable to a case of using the galvano scanner that accelerates and decelerates during the scanning with the illumination light, an acousto-optic deflector or a micro electro mechanical system, (MEMS) scanner in the main scanning direction.

Moreover, in Embodiments 2 and 3 described above, the scanning with the illumination light in the main scanning direction is performed by the scanning unit that accelerates and decelerates, while the scanning with the illumination light in the sub-scanning direction is performed by the scanning unit that performs uniform linear motion. However, the same effect can be achieved with a configuration in which these scanning units are switched to perform scanning by the uniform linear motion in the main scanning direction and scanning that accelerates and decelerates in the sub-scanning direction. Note that, in this case, with reference to the flowchart shown in FIG. 10, data is acquired at regular intervals in the sub-scanning direction in Steps S1004 and S1005. Therefore, in Step S1006 (and Step S1010), distortion is compensated in the main scanning direction.

Furthermore, in Embodiments 2 and 3 described above, in order to effectively suppress image distortion in the sub-scanning direction with a light computational load, data is selected at a data acquisition position located in the sub-scanning direction at the same position as the data generation position in the main scanning direction. However, data of at least two sampling points, which are simply closer, may be selected, irrespective of the direction such as the main scanning direction, from two fields in which data acquisition is performed continuously in chronological order. For example, FIG. 12 shows the example where the distance between the sampling points in the sub-scanning direction is shorter than that in the main scanning direction. The sampling points close to each other are limited to those on the same dashed-dotted line. However, if the dashed-dotted lines M1 and M2 are actually closer to each other, data of the black circles P12, P13, P33, and P32 may be set as candidates for obtaining data at the intersection position P22', for example, and data may be selected from among those candidates.

(Other Embodiment)

Note that, in the above embodiments, the description is given of the case where the present invention is applied to the SLO. However, the ophthalmic imaging apparatus to which the present invention is applied is not limited thereto. As described above, the present invention is also applicable to various other ophthalmic imaging apparatuses that scan the eye to be inspected with illumination light (measurement light) and acquire data to generate images, such as an AO-SLO apparatus and an optical coherence tomography (OCT) apparatus.

Moreover, in the above embodiments, the description is given of the case where the object to be inspected is the eye. However, the present invention is also applicable to an object to be inspected other than the eye, such as skin and organs. In this case, the present invention has an aspect of a medical device such as an endoscope, for example, other than the ophthalmic imaging apparatus. Therefore, it is preferable that the present invention is understood as an inspection apparatus illustrated as the ophthalmic imaging apparatus and that the eye to be inspected is understood as one aspect of the object to be inspected.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment (s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment (s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not, limited to the disclosed exemplary embodiments. The scope of the following claims is to be accorded the broadest interpretation so as to encompass all such modifications and equivalent structures and functions.

This application claims the benefit of Japanese Patent Application No. 2016-152565, filed Aug. 3, 2016 and Japanese Patent Application No. 2016-152781, filed Aug. 3, 2016 which are hereby incorporated by reference herein in their entirety.

What is claimed is:

1. An inspection apparatus comprising:
   a first scanning member that scans an object to be inspected by reciprocating scanning with illumination light in a main scanning direction;
   a second scanning member that scans the object to be inspected at a constant speed with the illumination light in a sub-scanning direction that intersects with the main scanning direction;
   a scanning control unit that allows the first and second scanning members to perform a 2D scan of the object to be inspected with the illumination light in a first field within a data acquisition area, and to perform a 2D scan of the object to be inspected in a second field different from the first field within the data acquisition area; and
   a data acquisition unit that acquires data of the object to be inspected based on the illumination light returned from the object to be inspected in the first and second fields, wherein
   the scanning control unit sets the second field by shifting a scanning start position of the 2D scan for the first field by a predetermined amount in the sub-scanning direction, and
   the predetermined amount is determined for the 2D scan with the illumination light such that the closer to the scanning center in the main scanning direction within the data acquisition area, the more regular the interval between the first and second fields in the sub-scanning direction.

2. The inspection apparatus according to claim 1, wherein the scanning center is a center in the main scanning direction in an attention area within the data acquisition area, and wherein the predetermined amount is determined such that at least two data acquisition positions in the first field and at least two data acquisition positions in the second field, which are lined up in the sub-scanning direction at the center in the main scanning direction in an attention area within the data acquisition area, are alternately arranged at regular intervals.

3. The inspection apparatus according to claim 2, wherein the attention area is in the center of the data acquisition area, and the center in the main scanning direction is the scanning center in the main scanning direction.

4. The inspection apparatus according to claim 1, wherein the first scanning member includes a mirror that reflects the illumination light and a member that drives the mirror so as to increase and decrease a scanning speed during scanning in the data acquisition area by reflecting the illumination light with the mirror.

5. The inspection apparatus according to claim 1, further comprising:
   a period detecting unit that detects a period of oscillation of the first scanning member, wherein
   the scanning control unit obtains the predetermined amount based on a scanning speed of the illumination light by the second scanning member and an output from the period detecting unit.

6. The inspection apparatus according to claim 5, further comprising:
   an amplitude detecting unit that detects an amplitude of oscillation of the first scanning member, wherein
   the data acquisition unit determines timing for acquiring the data, based on the output from the period detecting unit and an output from the amplitude detecting unit, such that data acquisition positions in the first and second fields for acquiring the data are arranged in a straight line extending in the sub-scanning direction.

7. The inspection apparatus according to claim 1, wherein the first scanning member is a resonant scanner.

8. An inspection apparatus comprising:
   a first scanning member that scans an object to be inspected by reciprocating scanning with illumination light in a main scanning direction;
   a second scanning member that scans the object to be inspected at a constant speed with the illumination light in a sub-scanning direction that intersects with the main scanning direction;
   a scanning control unit that allows the first and second scanning members to perform a 2D scan of the object to be inspected with the illumination light in a first field within a data acquisition area, and to perform a 2D scan of the object to be inspected in a second field different from the first field within the data acquisition area;
   a generation position setting unit that sets data generation positions for generating an image, the data generation positions being arranged at first intervals in the main scanning direction and at second intervals in the sub-scanning direction;
   an acquisition position setting unit that sets data acquisition positions, in the first and second fields, for acquiring data from the illumination light returned from the object to be inspected;
   a selecting unit that selects data acquired at least at two data acquisition positions located closest to each of the set data generation positions among the data acquisition positions set in the first and second fields; and
   an image generation unit that generates an image of the object to be inspected by using data at the data generation positions generated from the selected data.

9. The inspection apparatus according to claim 8, wherein the first interval is an interval between the data acquisition positions in the main scanning direction set by the acquisition position setting unit.

10. The inspection apparatus according to claim 8, wherein
the selecting unit selects data acquired at least at two data acquisition positions located closest to each of the set data generation positions, among the data acquisition positions arranged in the sub-scanning direction at the same positions in the main scanning direction as the data generation positions.

11. The inspection apparatus according to claim 8, wherein
the data selected by the selecting unit is data in the first and second fields in which data is acquired continuously in chronological order.

12. The inspection apparatus according to claim 8, wherein
the first scanning member includes a mirror that reflects the illumination light and a member that drives the mirror so as to increase and decrease a scanning speed during scanning in the data acquisition area by reflecting the illumination light with the mirror.

13. The inspection apparatus according to claim 8, further comprising:
a detecting unit that detects an amplitude and a period of oscillation of the first scanning member, wherein
the acquisition position setting unit sets the data acquisition positions based on an output from the detecting unit such that the data acquisition positions are arranged in a straight line extending in the sub-scanning direction in the first and second fields.

14. The inspection apparatus according to claim 8, wherein
the first scanning member is a resonant scanner.

15. A method for controlling an inspection apparatus including
a first scanning member that scans an object to be inspected by reciprocating scanning with illumination light in a main scanning direction,
a second scanning member that scans the object to be inspected at a constant speed with the illumination light in a sub-scanning direction that intersects with the main scanning direction, and
a scanning control unit that allows the first and second scanning members to perform a 2D scan of the object to be inspected with the illumination light in a first field within a data acquisition area, and to perform a 2D scan of the object to be inspected in a second field different from the first field within the data acquisition area,
the method comprising:
setting the second field by shifting a scanning start position of the 2D scan for the first field by a predetermined amount in the sub-scanning direction; and
acquiring data of the object to be inspected based on the illumination light returned from the object to be inspected in the first and second fields, wherein
the predetermined amount is determined for the 2D scan with the illumination light such that the closer to the scanning center in the main scanning direction within the data acquisition area, the more regular the interval between the first and second fields in the sub-scanning direction.

16. A non-transitory tangible medium having recorded thereon a program for causing a computer to perform steps of the method according to claim 15.

17. A method for controlling an inspection apparatus according to claim 15, wherein
the scanning control unit sets the second field by shifting a scanning start position of the 2D scan for the first field by a predetermined amount in the sub-scanning direction, and
the predetermined amount is determined for the 2D scan with the illumination light such that the closer to the scanning center in the main scanning direction within the data acquisition area, the more regular the interval between the first and second fields in the sub-scanning direction,
the method comprising:
setting the second field by shifting a scanning start position of the 2D scan for the first field by a predetermined amount in the sub-scanning direction; and
acquiring data of the object to be inspected based on the illumination light returned from the object to be inspected in the first and second fields, wherein
the predetermined amount is determined such that at least two data acquisition positions in the first field and at least two data acquisition positions in the second field, which are lined up in the sub-scanning direction at the center in the main scanning direction in an attention area within the data acquisition area, are alternately arranged at regular intervals.

18. A method for controlling an inspection apparatus including
a first scanning member that scans an object to be inspected by reciprocating scanning with illumination light in a main scanning direction,
a second scanning member that scans the object to be inspected at a constant speed with the illumination light in a sub-scanning direction that intersects with the main scanning direction, and
a scanning control unit that allows the first and second scanning members to perform a 2D scan of the object to be inspected with the illumination light in a first field within a data acquisition area, and to perform a 2D scan of the object to be inspected in a second field different from the first field within the data acquisition area,
the method comprising:
setting data generation positions for generating an image, which are arranged at first intervals in the main scanning direction and at second intervals in the sub-scanning direction;
setting data acquisition positions, in the first and second fields, for acquiring data from the illumination light returned from the object to be inspected;
selecting data acquired at least at two data acquisition positions located closest to each of the set data generation positions among the data acquisition positions set in the first and second fields; and
generating an image of the object to be inspected by using data at the data generation positions generated from the selected data.

* * * * *